United States Patent
Miller et al.

(10) Patent No.: US 11,484,306 B2
(45) Date of Patent: *Nov. 1, 2022

(54) APPARATUS AND METHODS FOR OCCLUSION OF BLOOD VESSELS

(71) Applicant: Amsel Medical Corporation, Cambridge, MA (US)

(72) Inventors: Arnold Miller, Cambridge, MA (US); Avraham Ram Lore, Kiryat Tivon (IL); Raanan Miller, Cambridge, MA (US); Nir Lilach, Kfar Yehoshua (IL); William Edelman, Sharon, MA (US)

(73) Assignee: AMSEL MEDICAL CORPORATION, Cambridge, MA (US)

( * ) Notice: Subject to any disclaimer, the term of this patent is extended or adjusted under 35 U.S.C. 154(b) by 85 days.

This patent is subject to a terminal disclaimer.

(21) Appl. No.: 16/856,593

(22) Filed: Apr. 23, 2020

(65) Prior Publication Data
US 2020/0253603 A1   Aug. 13, 2020

Related U.S. Application Data

(63) Continuation-in-part of application No. 15/906,763, filed on Feb. 27, 2018, now Pat. No. 10,820,895, and (Continued)

(51) Int. Cl.
*A61B 17/128* (2006.01)
*A61B 17/122* (2006.01)
(Continued)

(52) U.S. Cl.
CPC ...... *A61B 17/064* (2013.01); *A61B 17/00008* (2013.01); *A61B 17/0682* (2013.01);
(Continued)

(58) Field of Classification Search
CPC . A61B 17/0057; A61B 17/0644; A61B 17/12; A61B 17/12009; A61B 17/122; A61B 17/128; A61B 17/1285; A61B 2017/00575; A61B 2017/00579; A61B 2017/00584; A61B 2017/00588; A61B 2017/00592; A61B 2017/00615; A61B 2017/00619; A61B 2017/00623; A61B 2017/00632; A61B 2017/0641;
(Continued)

(56) References Cited

U.S. PATENT DOCUMENTS

| | | | |
|---|---|---|---|
| 6,312,446 B1 * | 11/2001 | Huebsch | A61B 17/0057 606/157 |
| 2008/0208226 A1 * | 8/2008 | Seibold | A61B 17/0057 606/158 |

(Continued)

*Primary Examiner* — Martin T Ton

(57) ABSTRACT

Apparatus and methods are provided for occluding blood vessels and other anatomical structures. Occlusion devices are delivered percutaneously and extraluminally through a small gauge needle and include expandable elements that are deployable on opposite sides of a target vessel to be occluded. When positioned about the vessel the elements are expanded and brought together to compress and occlude the vessel. Embodiments include those adapted for temporary as well as permanent use.

6 Claims, 39 Drawing Sheets

Related U.S. Application Data a continuation-in-part of application No. 15/044,323, filed on Feb. 16, 2016, now Pat. No. 10,631,870, said application No. 15/906,763 is a continuation-in-part of application No. 14/639,814, filed on Mar. 5, 2015, now Pat. No. 9,936,955, and a continuation-in-part of application No. 14/272,304, filed on May 7, 2014, now Pat. No. 10,076,339, and a continuation-in-part of application No. 13/857,424, filed on Apr. 5, 2013, now abandoned, and a continuation of application No. 13/348,416, filed on Jan. 11, 2012, now abandoned, said application No. 15/044,323 is a continuation of application No. 13/857,424, filed on Apr. 5, 2013, now abandoned, and a continuation of application No. 13/348,416, filed on Jan. 11, 2012, now abandoned.

(60) Provisional application No. 62/084,989, filed on Nov. 26, 2014, provisional application No. 61/948,241, filed on Mar. 5, 2014, provisional application No. 61/620,787, filed on Apr. 5, 2012, provisional application No. 61/431,609, filed on Jan. 11, 2011.

(51) Int. Cl.
  *A61B 17/12* (2006.01)
  *A61B 17/064* (2006.01)
  *A61B 17/00* (2006.01)
  *A61B 17/068* (2006.01)
  *A61B 17/04* (2006.01)

(52) U.S. Cl.
  CPC ............ *A61B 17/12* (2013.01); *A61B 17/122* (2013.01); *A61B 17/128* (2013.01); *A61B 17/12009* (2013.01); *A61B 17/12013* (2013.01); *A61B 17/1214* (2013.01); *A61B 17/12022* (2013.01); *A61B 17/12027* (2013.01); *A61B 17/12031* (2013.01); *A61B 17/12036* (2013.01); *A61B 17/1285* (2013.01); *A61B 17/12145* (2013.01); *A61B 17/0643* (2013.01); *A61B 2017/00668* (2013.01); *A61B 2017/00867* (2013.01); *A61B 2017/00893* (2013.01); *A61B 2017/00986* (2013.01); *A61B 2017/0419* (2013.01); *A61B 2017/0641* (2013.01); *A61B 2017/0645* (2013.01); *A61B 2017/12054* (2013.01); *A61B 2017/12095* (2013.01)

(58) Field of Classification Search
  CPC ........... A61B 2017/12004; A61F 6/204; A61F 6/206; A61F 6/208
  USPC .......................................... 606/158
  See application file for complete search history.

(56) References Cited

U.S. PATENT DOCUMENTS

| | | | |
|---|---|---|---|
| 2009/0084386 A1* | 4/2009 | McClellan | A61F 6/225 128/831 |
| 2013/0046331 A1* | 2/2013 | Christensen | A61B 17/12036 606/200 |
| 2017/0095257 A1* | 4/2017 | Miller | A61B 17/0643 |

* cited by examiner

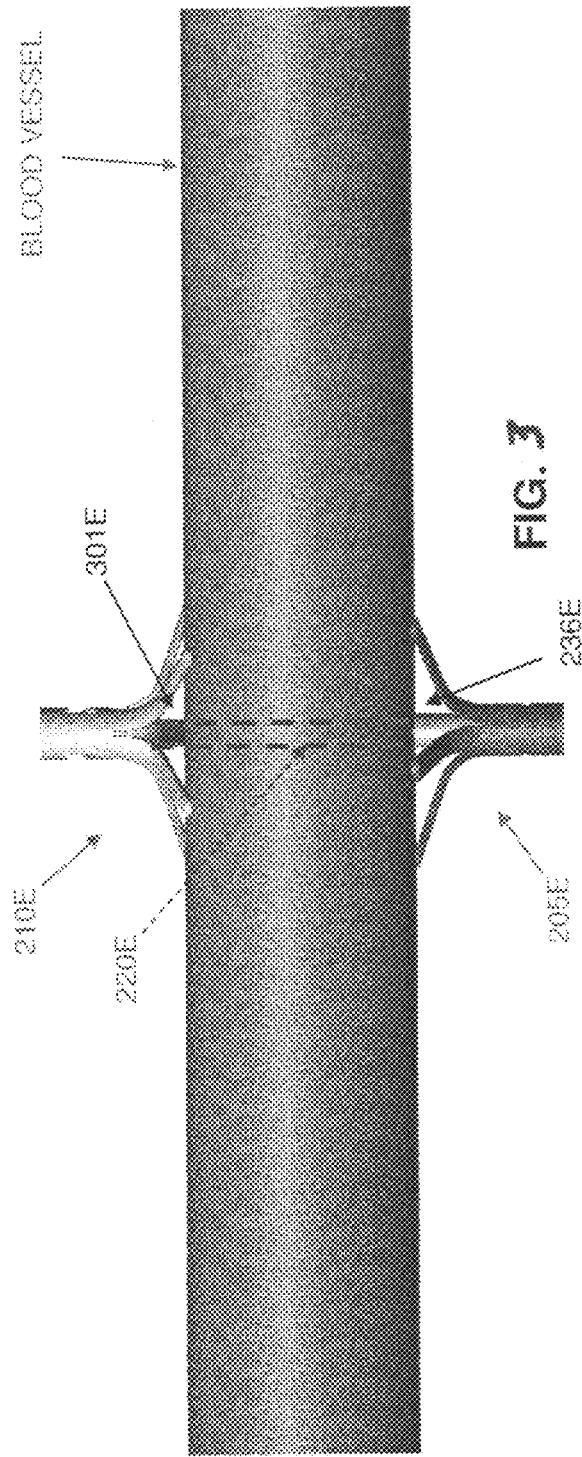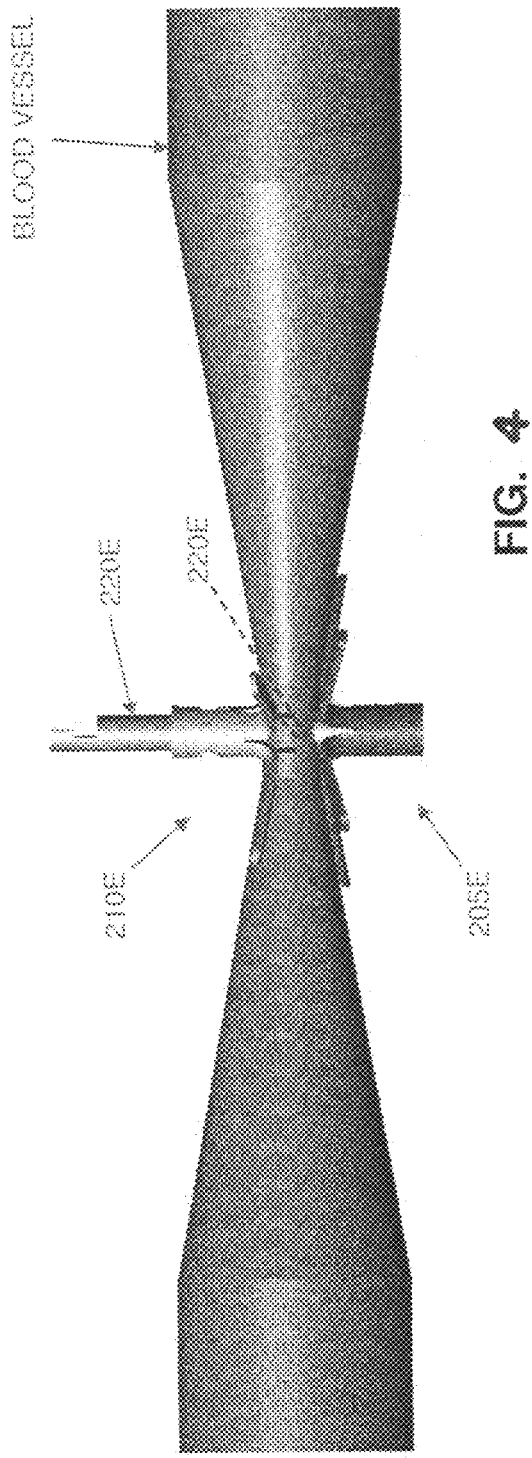

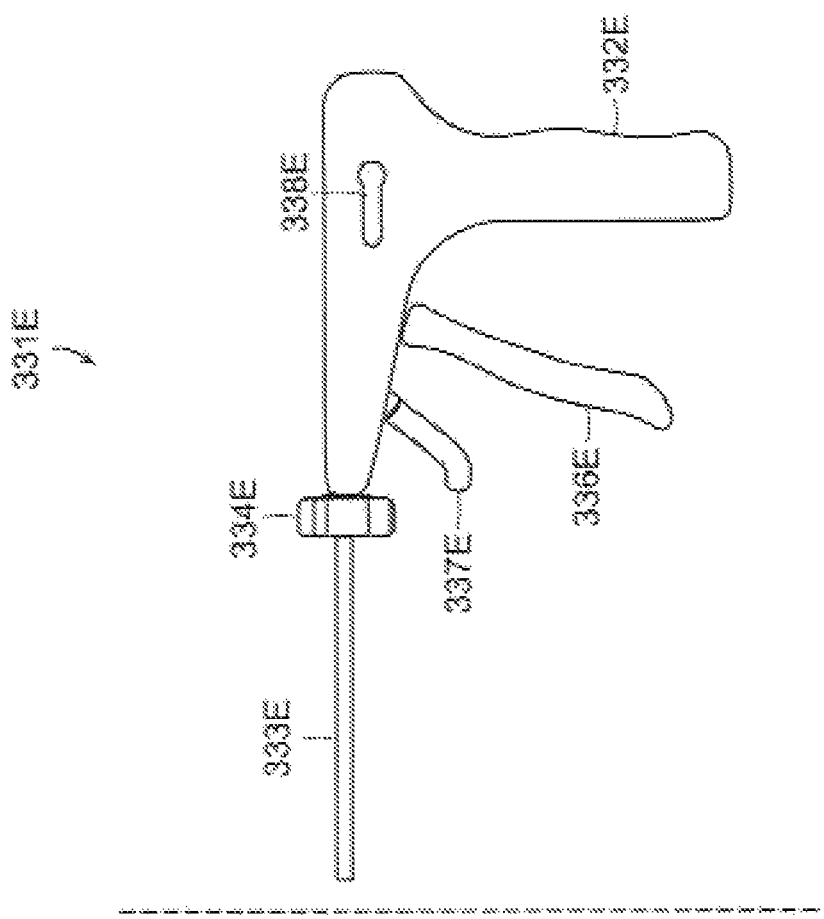
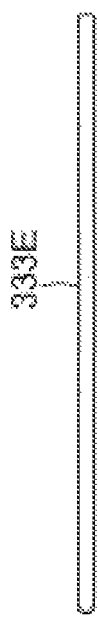
FIG. 7

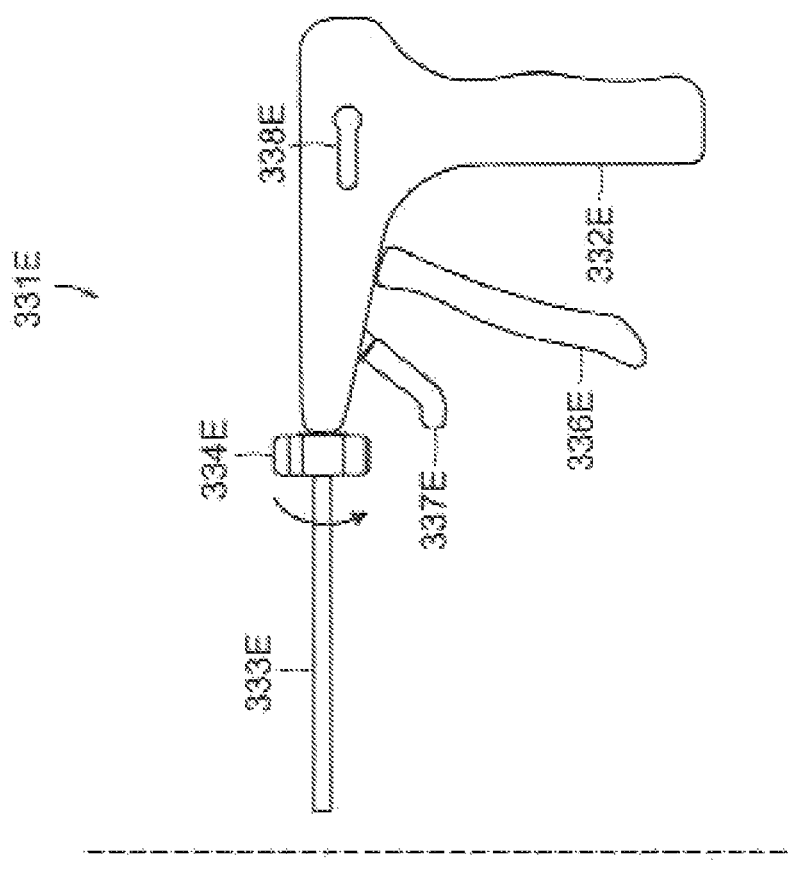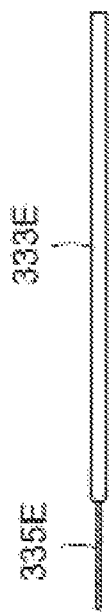
FIG. 8

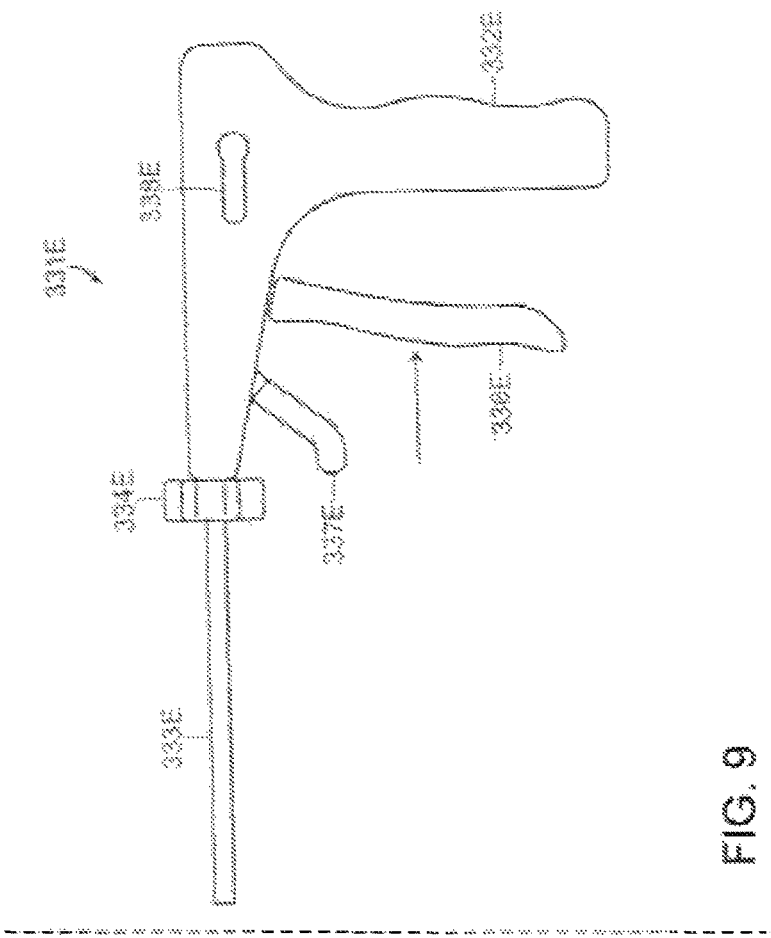
FIG. 9
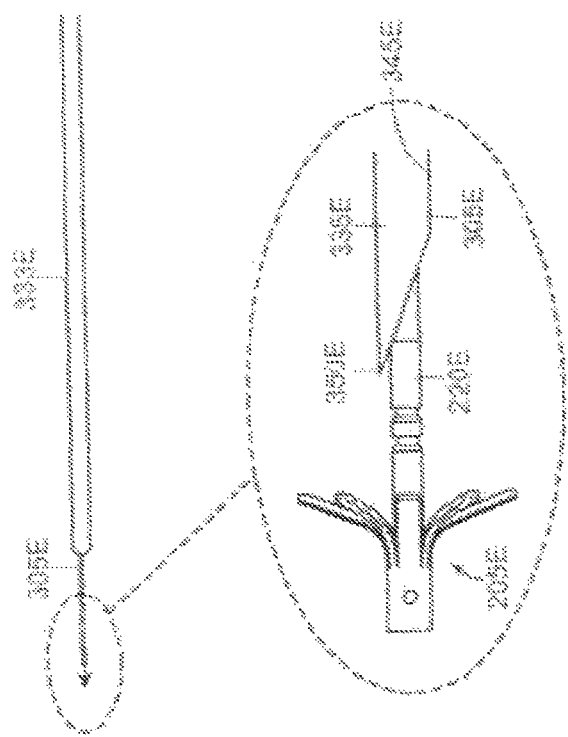

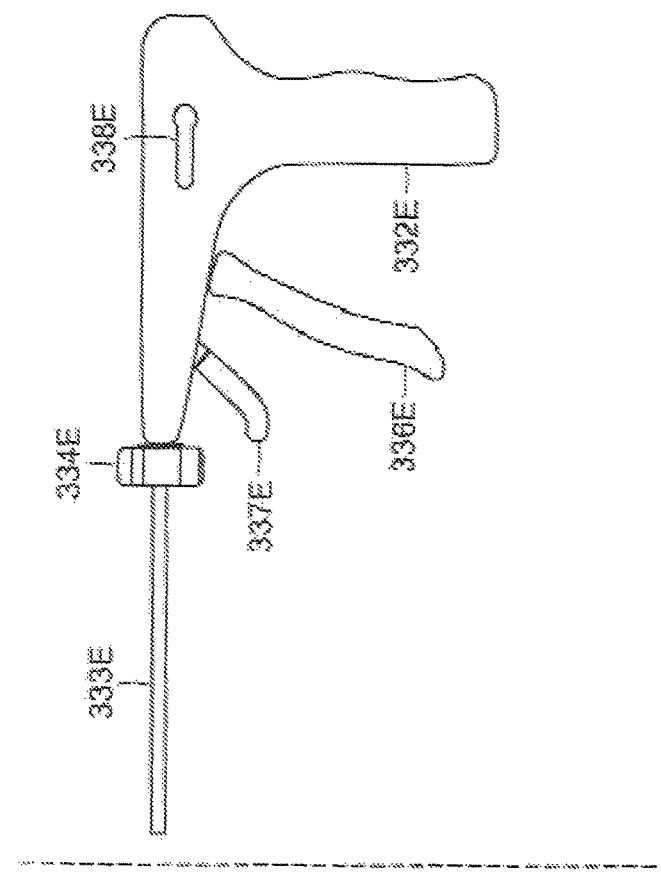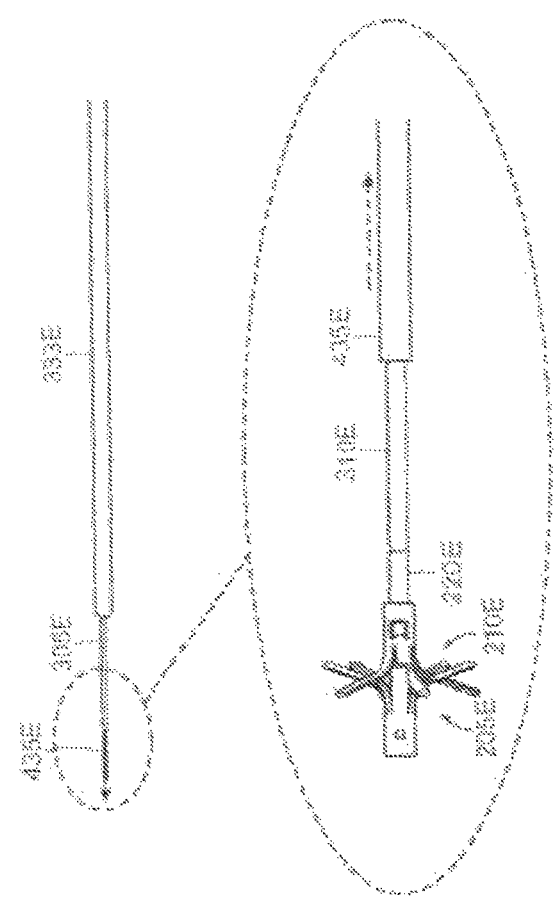
FIG. 12

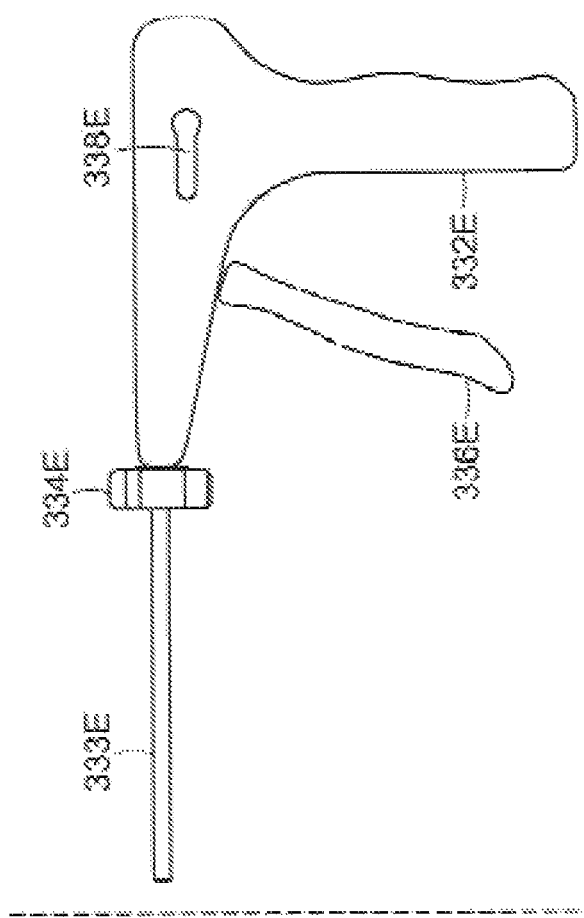
FIG. 15

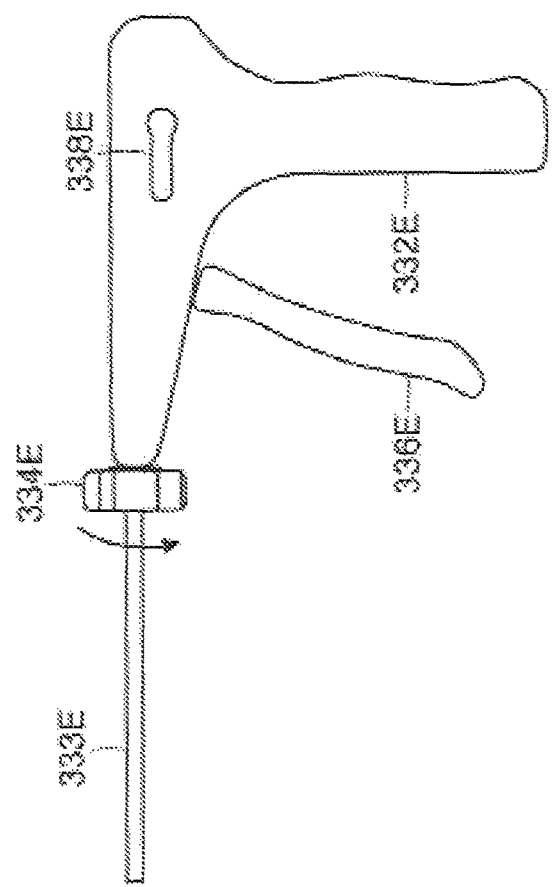
FIG. 16

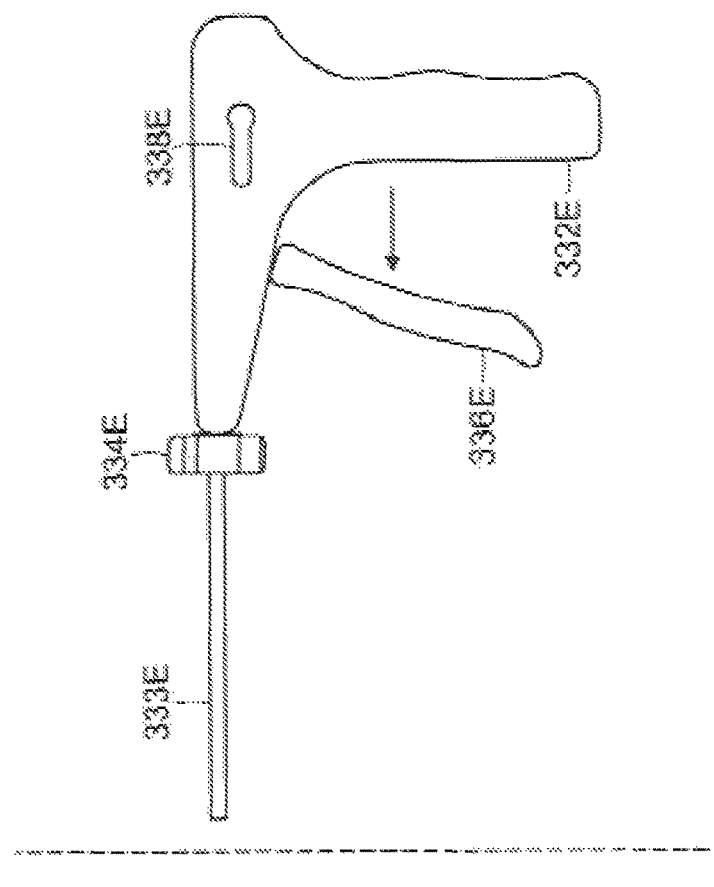
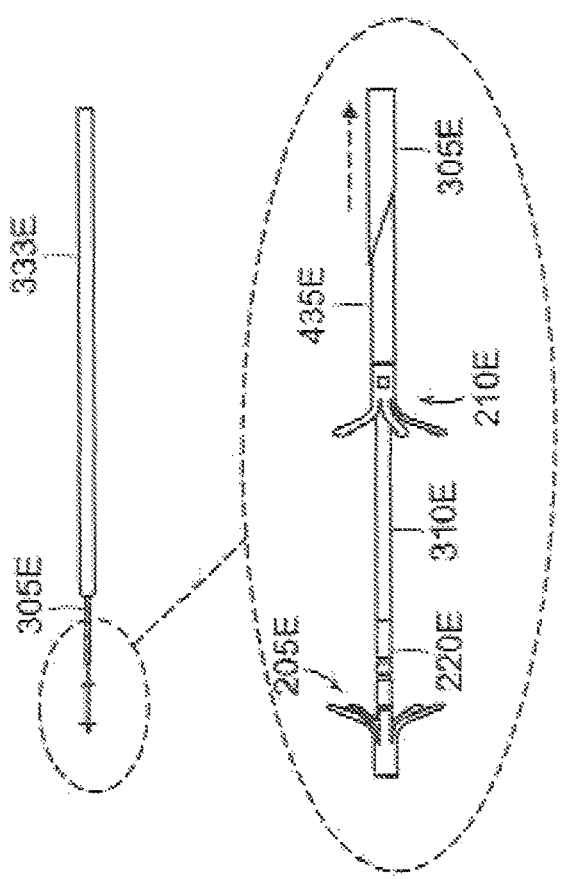
FIG. 18

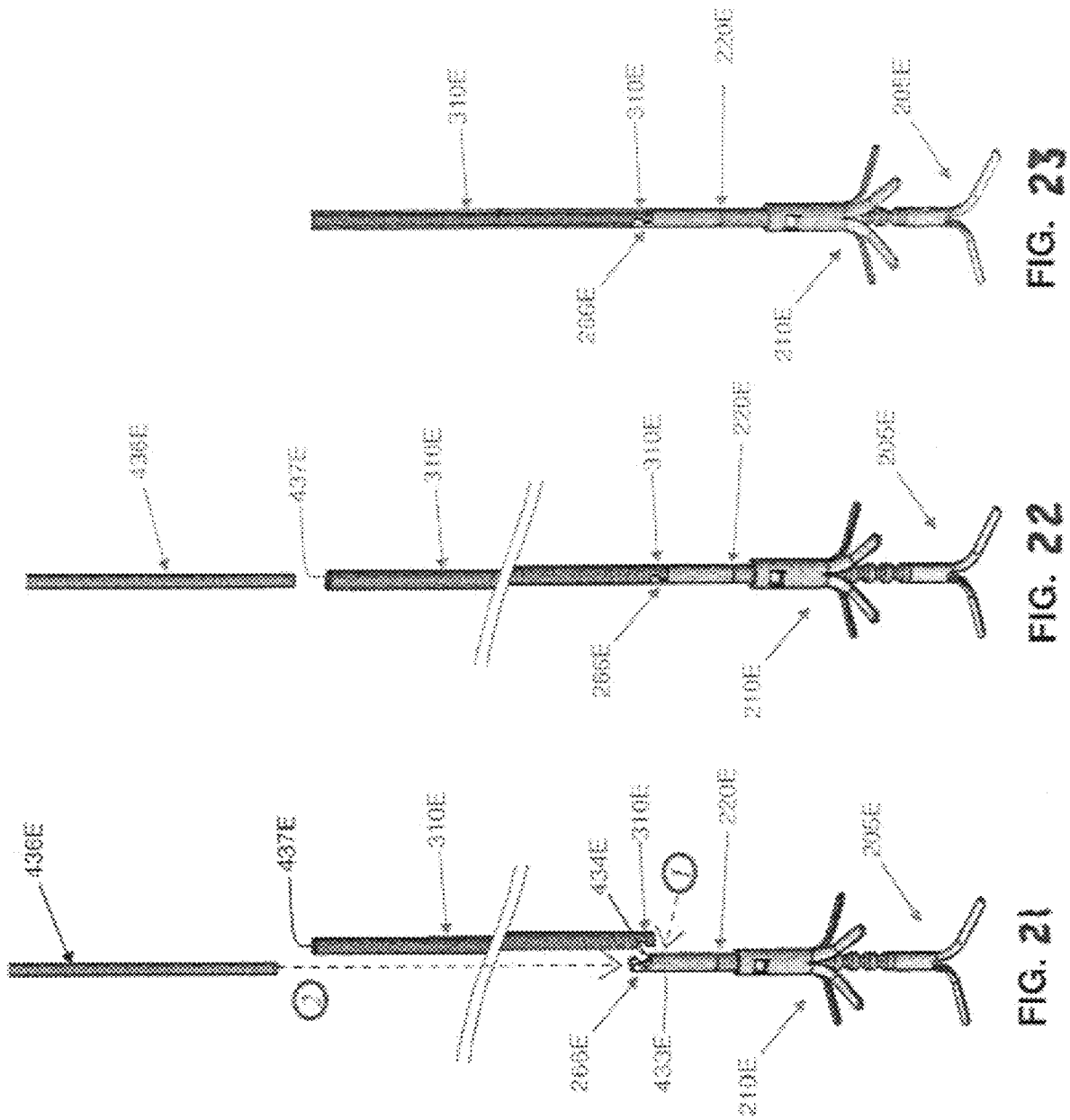

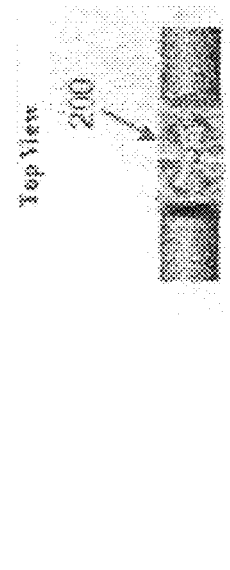
FIG. 32
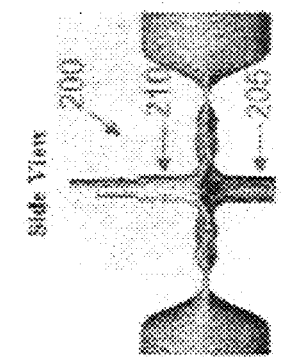
FIG. 34
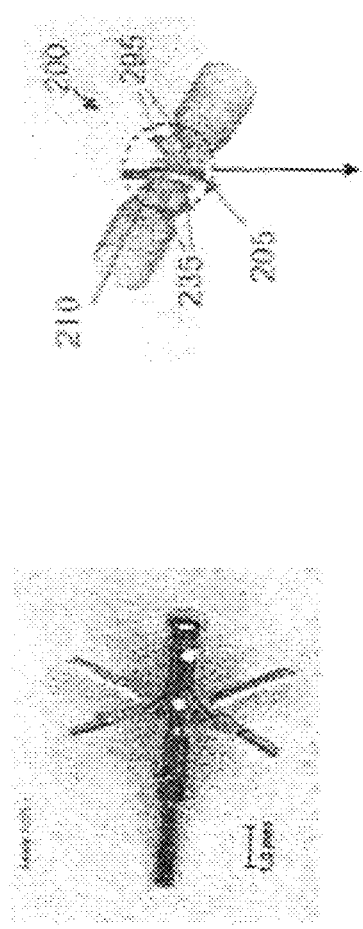
FIG. 31
FIG. 30
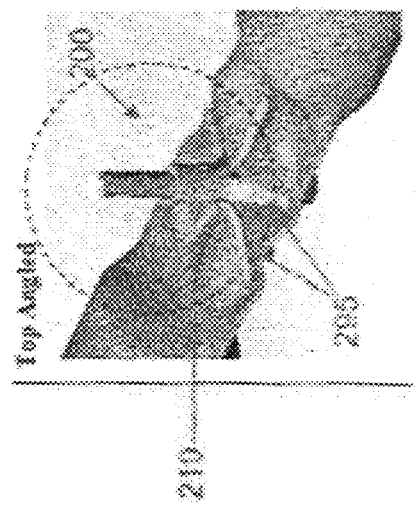
FIG. 33

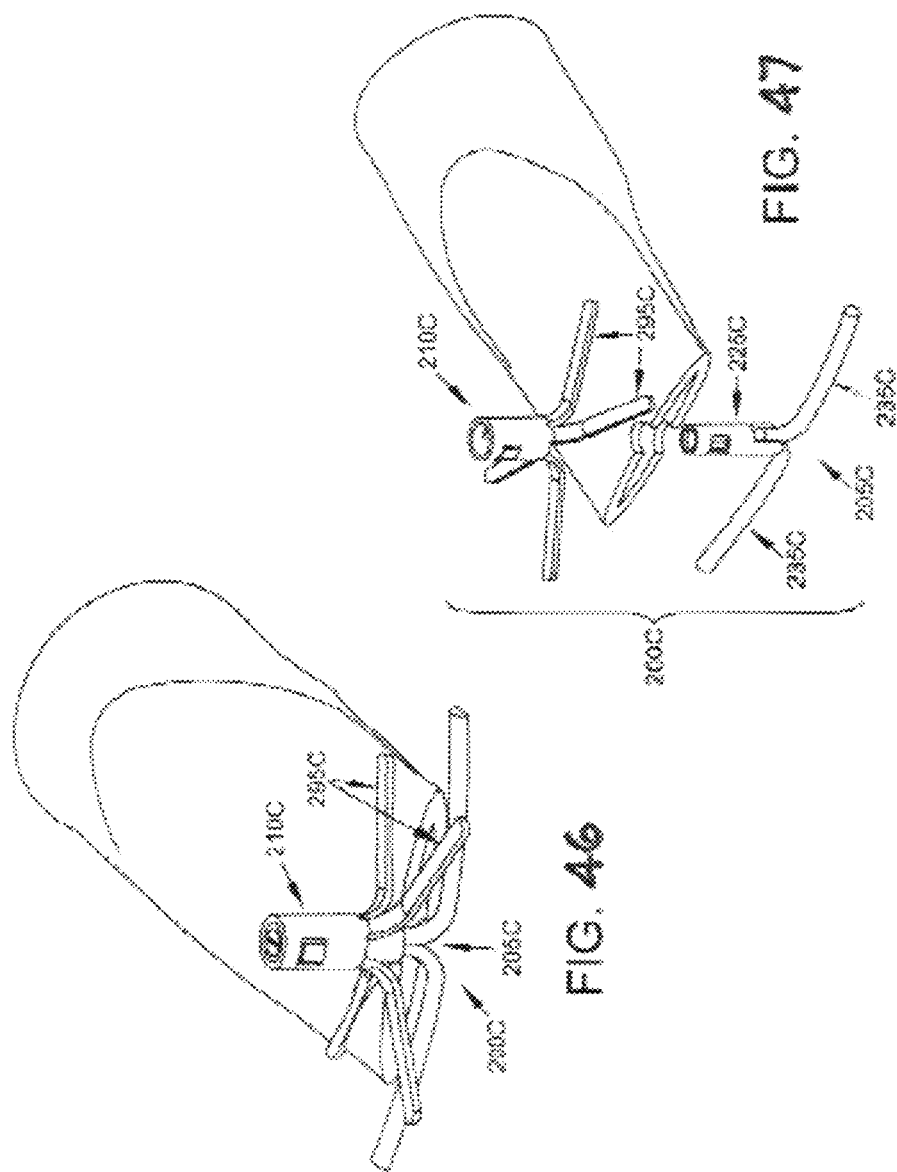

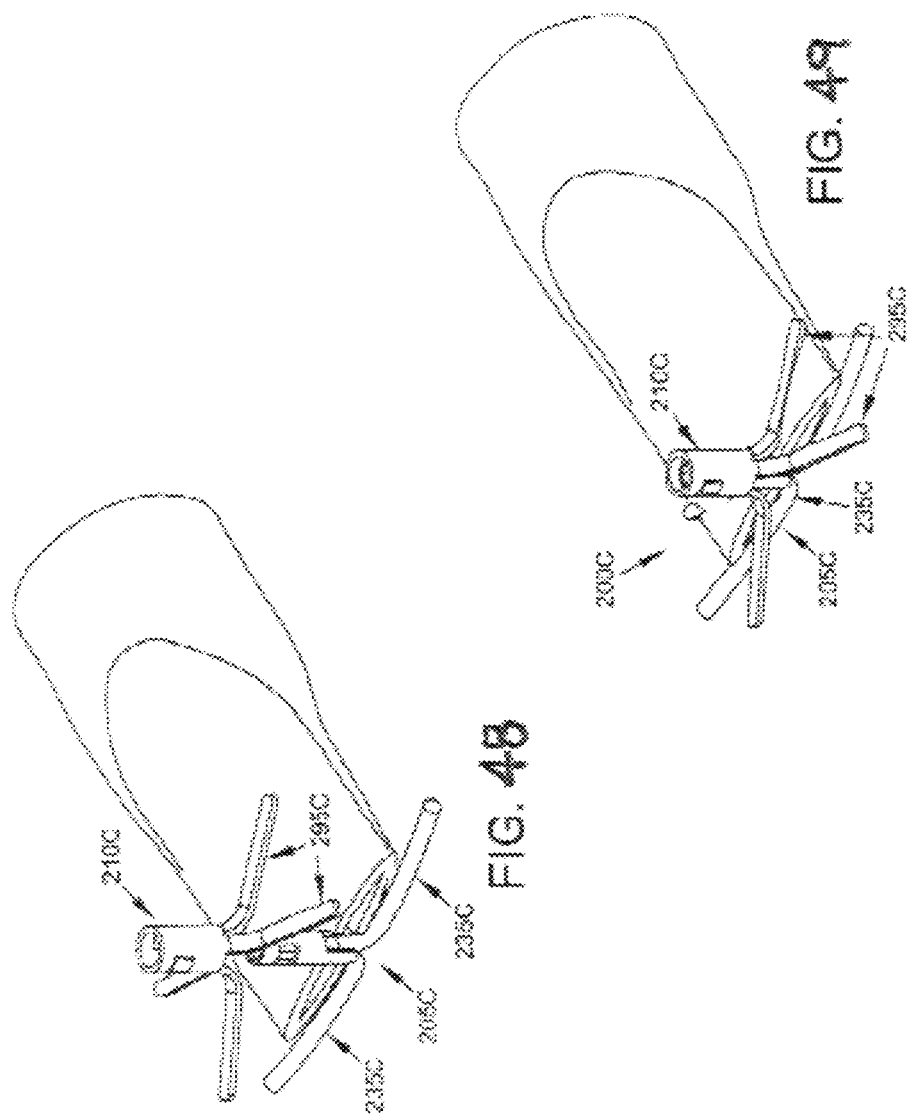

APPARATUS AND METHODS FOR OCCLUSION OF BLOOD VESSELS

This patent application:

(i) is a continuation-in-part of prior U.S. patent application Ser. No. 15/044,323, filed Feb. 16, 2016, now U.S. Pat. No. 9,936,955, issued Sep. 16, 2018 which is a continuation of prior application Ser. No. 13/857,424, filed Apr. 5, 2013, which claims priority to U.S. Provisional Application Ser. No. 61/620,787, filed Apr. 5, 2012 and is a continuation-in-part of prior application Ser. No. 13/348,416, filed Jan. 11, 2012 which patent application claims benefit of prior U.S. Provisional Patent Application Ser. No. 61/431,609, filed Jan. 11, 2011 and (ii) is a continuation-in-part of prior U.S. patent application Ser. No. 15/906,763, filed Feb. 27, 2018 which is a continuation-in-part of prior U.S. patent application Ser. No. 14/639,814, now U.S. Pat. No. 9,936,955 issued Apr. 10, 2018, which claims priority from U.S. Provisional Patent Application 62/084,989 filed Nov. 26, 2014, and is a continuation-in-part of prior U.S. patent application Ser. No. 14/272,304, filed May 7, 2014 which claims priority from U.S. Provisional Patent Application Ser. No. 61/948,241, filed Mar. 5, 2014 and Ser. No. 61/820,589, filed May 5, 2013 and is a continuation-in-part of prior U.S. application Ser. No. 13/857,424, filed Apr. 5, 2013 which claims priority from U.S. Provisional Patent Application Ser. No. 61/620, 787, filed Apr. 5, 2012 and which claims priority from prior U.S. application Ser. No. 13/348,416, filed Jan. 11, 2012 which patent application claims benefit of prior U.S. Provisional Patent Application Ser. No. 61/431,609, filed Jan. 11, 2011

The entire disclosures of the twelve (12) above-identified patent applications are hereby incorporated herein by reference.

FIELD OF THE INVENTION

This invention relates to surgical methods and apparatus in general, and more particularly to surgical methods and apparatus for the occlusion of blood vessels.

BACKGROUND OF THE INVENTION

There are numerous instances in medical practice in which it is necessary or desirable to fully or partially occlude a blood vessel, for example, in treatment of varicose veins or to close off an artery or to minimize blood loss caused by a traumatic injury, among others. It would be desirable to provide improved devices and techniques to effect these and other occlusive procedures.

SUMMARY OF THE INVENTION

The present invention provides a new and improved approaches for occluding blood vessels.

More particularly, in one aspect, the present invention provides extraluminally expandable needle-deliverable occlusion devices that may be used to treat varicose veins by occluding a target vein percutaneously using a minimally-invasive approach, with visualization of the target being provided by ultrasound and/or other visualization apparatus (e.g., CT, MRI, X-ray etc.). The occlusion devices can be delivered through a small gauge needle (e.g., 18 gauge or smaller) As a result treatment of varicose veins can be provided in a physician's office with local anesthetic and minimal post-operative care.

In another aspect of the invention, as when treating a trauma patient to prevent excessive blood loss, expandable occlusion devices, pre-loaded in a hypodermic needle, can be extraluminally deployed in proximity to a target arterial or venous site to effect localized compression to the vessel. The occlusion devices may be self-expandable upon release from the delivery needle or may be in a form that requires an additional step to expand the occlude (e.g., balloon inflation)

In one form of the invention, the occluder is configured so that at least a portion of the may assume (i) a diametrically-reduced configuration for disposition within the lumen of a delivery tube, such as a small (18 gauge or smaller) hypodermic needle and (ii) a diametrically-expanded configuration for disposition adjacent to the blood vessel, such that when said at least a portion of the occluder is in its diametrically-expanded configuration adjacent to the blood vessel, the occluder may cause occlusion of the blood vessel.

In another aspect of the invention, there is provided a method for occluding a blood vessel, in which an occlusion device as described above is positioned at a target site in proximity to or in engagement with a blood vessel to cause full or partial occlusion of the vessel.

In some aspects of the invention, the occluder may comprise two cooperating, separately deployable components and in other aspects the occlusion device may have a single expandable component.

In another aspect of the invention, there is provided an occluder that, after deployment may thereafter be reversed in full or in part so as to completely or partially restore the hollow structure to its original condition.

BRIEF DESCRIPTION OF THE DRAWINGS

The various features of the invention may be more fully appreciated from the following description, with reference to the accompanying drawings in which:

FIGS. 1-4 are schematic views showing a two-part occluder formed in accordance with the present invention;

FIGS. 5-13 are schematic views showing an installation apparatus for deploying the two-part occluder shown in FIGS. 1-4;

FIGS. 14-20 are schematic views showing another installation apparatus for deploying the two-part occluder shown in FIGS. 1-4;

FIGS. 21-23 are schematic views showing means for securing a two-part occluder to another installation apparatus;

FIGS. 30-35 illustrate the manner in which a two part fastener with interdigitated legs can constrain tissue and/or non-tissue layers in a serpentine configuration that circumscribes the fastener;

FIGS. 46-49 illustrate another embodiment of the two-part fastener;

DESCRIPTION OF THE ILLUSTRATIVE EMBODIMENTS

Figure 1:
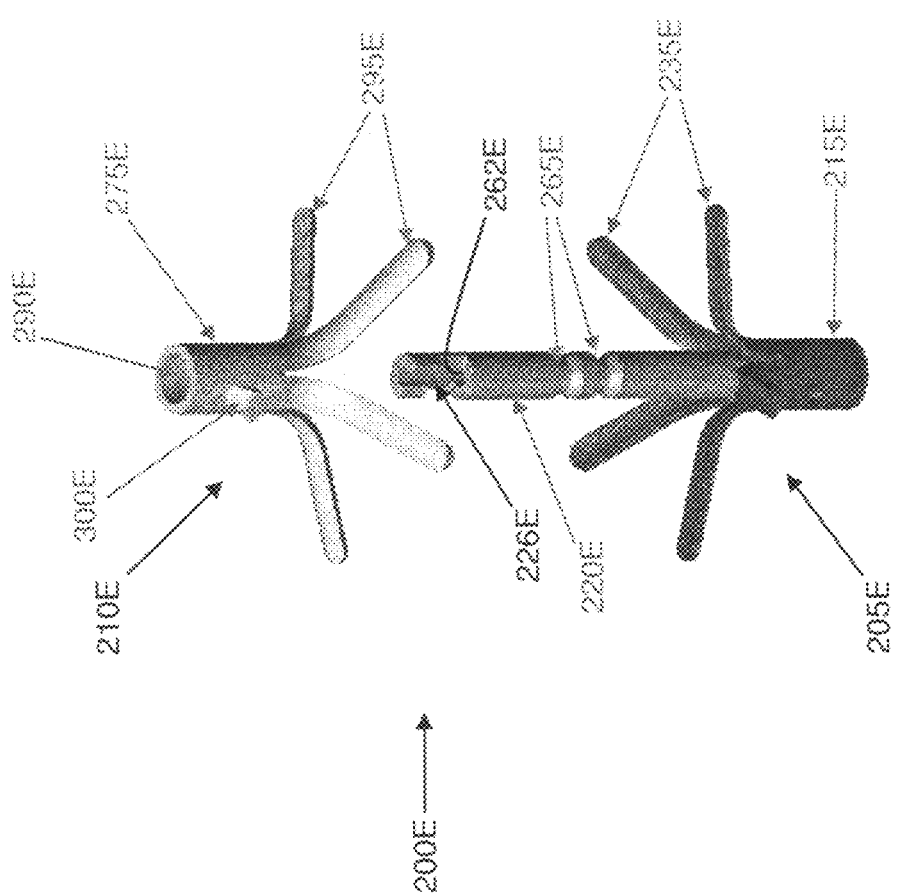
Figure 2:
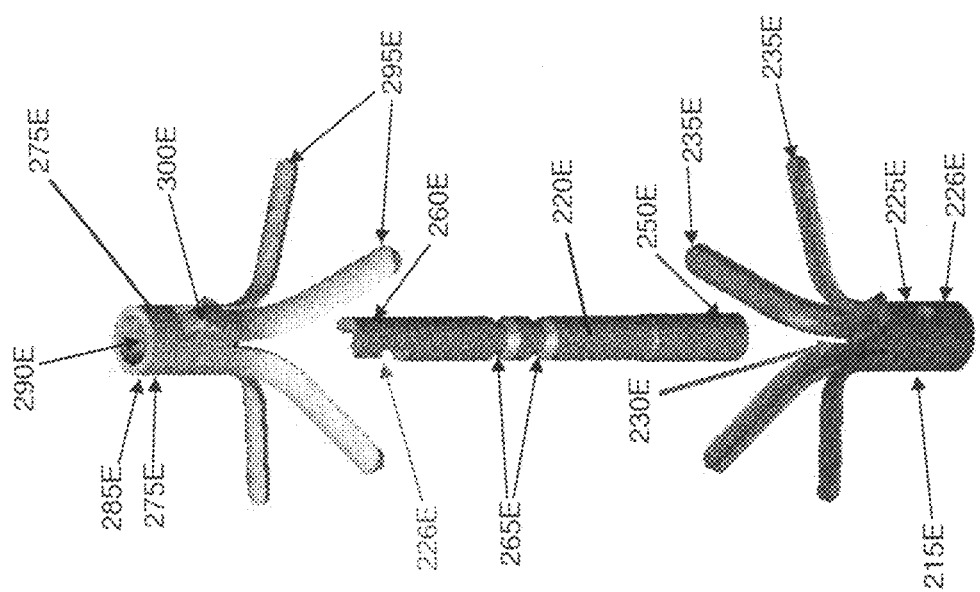
Figure 5:
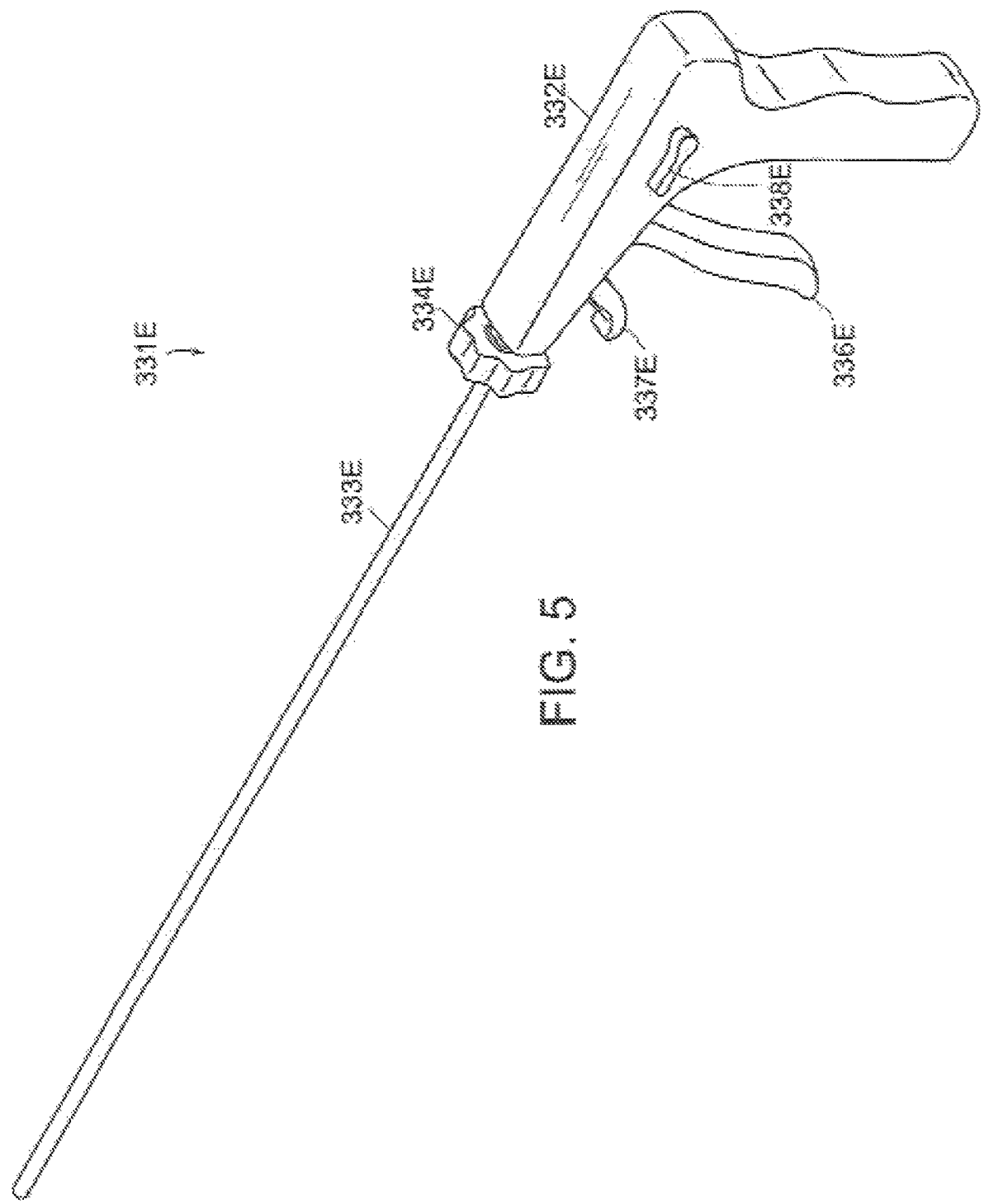
Figure 6:
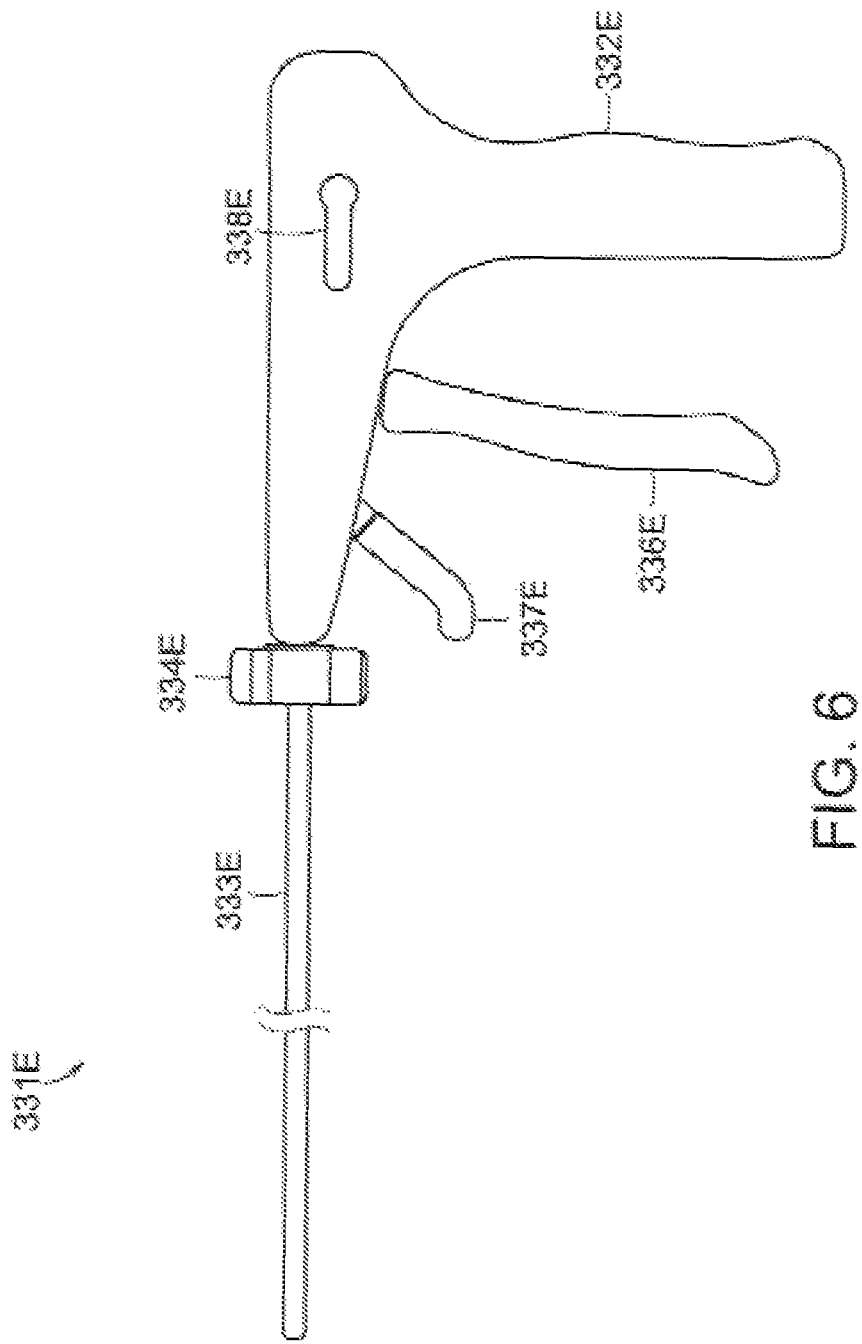

FIGS. 1-4 illustrate a two-part fastener 200E formed in accordance with the present invention. Two-part fastener 200E generally comprises a distal implant 205E and a proximal implant 210E.

Distal implant 205E comprises a distal implant body 215E and a distal implant locking tube 220E. Distal implant body 215E comprises a tube 225E having a proximal end 226E and an opposing distal end. Preferably distal implant 205E has a lumen 230E extending distally from its proximal end. Lumen 230E may extend along the entire length of distal implant body 215E or it may terminate short of the distal end of distal implant body 215E. By way of example but not limitation, where two-part fastener 200E is to be set over a guidewire, lumen 230E extends along the entire length of distal implant body 215E to accommodate a guidewire. The proximal end of the tube 225E is slit along its length to define a plurality of legs 235E. Distal implant body 215E is preferably formed at least in part out of an elastic material (e.g., a shape memory material having superelastic properties such as Nitinol or superelastic polymers, including superelastic plastics) and is constructed so that its legs 235E normally project laterally away from the longitudinal axis of tube 225E (e.g., in the manner shown in FIGS. 1-4), however, due to the elastic nature of the material used to form at least the legs 235E of distal implant body 215E, legs 235E can be constrained inwardly (e.g., to be contained within the lumen of a delivery needle, as discussed below) so that distal implant body 215E can assume a substantially linear, tubular disposition (in which case the of legs 235E converge to form the aforementioned proximal end of distal implant body 215E). However, when the constraint is removed (e.g., as when distal implant is deployed out of the delivery needle), the elastic nature of the material used to form at least the legs 235E of distal implant body 215E causes legs 235E to assume the position shown in FIGS. 1-4.

In one form of the invention, and as seen in FIGS. 1-4, legs 235E of distal implant 205E extend at an acute angle to the longitudinal axis of distal implant 205E, such that legs 235E collectively define a concave region 236E (FIG. 3).

Distal implant locking tube 220E has a distal end 250E and a proximal end 260E. Preferably distal implant locking tube 220E has a lumen 262E extending distally from proximal end 260E. Lumen 262E may extend along the entire length of distal implant locking tube 220E or it may terminate short of the distal end of distal implant locking tube 220E. By way of example but not limitation, where two-part fastener 200E is to be set over a guidewire, lumen 262E of distal implant locking tube 220E extends along the entire length of distal implant locking tube 220E. In the embodiment of FIGS. 1-4 a set of circumferential grooves or recesses 265E may be formed in distal implant locking tube 220E, with the grooves or recesses 265E being disposed intermediate distal end 250E and proximal end 260E. Distal implant locking tube 220E may have, at its proximal end, a first half 266E of a mechanical interlock for releasably connecting distal implant locking tube 220E (and hence distal implant 205E) to a distal implant delivery tube 310E, described below. Distal implant locking tube 220E is preferably formed out of a biocompatible material which is relatively inelastic along its length, whereby to minimize lengthwise stretching, although it may be somewhat flexible, whereby to allow it to be delivered over a curved path. By way of example but not limitation, distal implant locking tube 220E may be formed out of a titanium alloy such as Ti 5 AL-4V.

Distal implant locking tube 220E is disposed within, and extends proximally from, lumen 230E of distal implant body 215E. Distal implant locking tube 220E is secured to distal implant body 215E in ways well known in the art (e.g., by spot welding, adhesives, mechanical interlocks, etc.), whereby to collectively form a singular structure. Note that by forming distal implant body 215E out of an elastic material, and by forming distal implant locking tube 220E out of a material which is relatively inelastic along its length, distal implant body 215E is easily deformable (e.g., so that its legs 235E can be constrained within a delivery needle) while distal implant locking tube 220E is fixed in configuration (e.g., so that it can serve to hold proximal implant 210E to distal implant 205E, as discussed below.

Proximal implant 210E may be formed in a manner similar to distal implant 205E and comprises a tube 275E having a distal end, a proximal end 285E, and a lumen 290E extending therebetween. Tube 275E is slit at its distal end so as to define a plurality of legs 295E. A set of inwardly-projecting tangs 300E may be formed in tube 275E, between legs 295E and proximal end 285E, for engaging the aforementioned grooves or recesses 265E in distal implant locking tube 220E, when the implants are connected together. If desired, the locations and configurations of grooves or recesses 265E and tangs 300E can be reversed, i.e., outwardly-projecting tangs 300E can be provided on distal implant locking tube 220E and grooves or recesses 265E can be provided on the inner side wall of tube 275E, or other means can be provided for connecting tube the proximal implant 210E to distal implant. Proximal implant 210E is preferably formed at least in part out of an elastic material (e.g., a shape memory material having superelastic properties such as Nitinol) and constructed so that, when unstressed, its legs 295E normally project laterally away from the longitudinal axis of tube 275E (e.g., in the manner shown in FIGS. 1-4), however, legs 295E can be constrained inwardly so that proximal implant 210E can assume a substantially linear, tubular configuration containable in the lumen of a delivery needle (with the constrained of legs 295E collectively forming the distal end of proximal implant 210E). However, when the constraint is removed, the elastic nature of the material used to form at least the legs 295E of proximal implant 210E causes legs 295E to return to the position shown in FIGS. 1-4.

In the form of the invention shown in FIGS. 1-4, legs 295E of proximal implant 210E extend at an obtuse angle to the longitudinal axis of proximal implant 210E, such that legs 295E collectively define a concave region 301E.

Similarly, in the distal implant of the embodiment of FIGS. 1-4, the legs also define a concave region 236E that is the reverse of the concavity of concave region 301E of proximal implant 210E so that the concavities of the proximal and distal implants face each other.

In the embodiment of FIGS. 1-4, distal implant 205E and proximal implant 210E are configured and sized so that distal implant locking tube 220E of distal implant 205E can be received in lumen 290E of proximal implant 210E to connect the implants together. The arrangement of tabs and grooves of the proximal and distal implants, permit some degree of rotational freedom of the connected implants so that the legs of the proximal and distal implants can self-adjust to be out of registry to allow the legs of the implants to interdigitate, resulting in a desirable mode of clamping action, described below. The circumferential grooves or recesses 265E of distal implant locking tube 220E and inwardly-projecting tangs 300E of proximal implant 210E are positioned so that they permit some variation in the degree to which the tissue layers are clamped together.

FIGS. 5-13 illustrate a delivery device for percutaneously deploying the two-part fastener. In this embodiment of the invention, the delivery device includes a hollow needle 305E (FIG. 9) for penetrating tissue, a distal implant delivery tube 310E (FIG. 10) for delivering distal implant 205E through hollow needle 305E to the far side of the blood vessel (or other tubular structure) which is to be occluded, and a proximal implant delivery tube 330E (FIG. 10) for delivering proximal implant 210E for mating with distal implant 205E The delivery device may be suitable for use in a number of circumstance, including use in laparoscopic procedures. The delivery device 331E may comprise a handle 332E, an outer sheath 333E, a knob 334E, a first trigger 336E, a second trigger 337E and a release lever 338E, with the functionality as described below.

More particularly, hollow needle 305E (FIG. 9) has a distal end 335E, a proximal end (not shown, but contained within laparoscopic device 331E) and a lumen 345E. Distal end 335E of hollow needle 305E terminates in a sharp point 350E.

Distal implant delivery tube 310E (FIG. 10) comprises a distal end 360E and a proximal end (not shown, but contained within laparoscopic device 331E). Distal end 360E of distal implant delivery tube 310E also comprises a second half 361E of a mechanical interlock that may be complementary to the first half 266E on the proximal end of locking tube 220E for releasably securing the distal end of distal implant delivery tube 310E to the proximal end of distal implant 205E (FIGS. 21-23). It should be understood that other arrangements for releasably connecting the distal implant delivery tube to the distal implant may be employed such as a threaded connection.

Proximal implant delivery tube 330E (FIG. 10) comprises a distal end 435E, a proximal end (not shown, but contained within laparoscopic device 331E) and a lumen 445E extending therebetween.

Two-part fastener 200E and its delivery device 331E) are preferably used as follows.

First, the sheath of delivery device is inserted percutaneously to position the distal end of the sheath 333E adjacent the occlusion site, preferably while hollow needle 305E contained within the sheath (FIG. 7). Then sheath 333E is retracted to expose the needle, e.g., by turning knob 334E (FIG. 8), and hollow needle 305E is advanced across and through the opposing walls of the blood vessel or other target hollow anatomical structure which is to be occluded to position the tip of the needle and the distal implant within the needle distally of the vessel.

Next, hollow needle 305E is retracted proximally, back across the blood vessel, e.g., via first trigger 336E (FIG. 9) while maintaining the position of the distal implant with the distal implant delivery tube 310E, thus deploying the distal implant out of the needle and distally of the vessel. This action allows legs 235E of distal implant 205E to expand radially on the far side of the blood vessel. At this point, distal implant locking tube 220E extends proximally through the blood vessel.

Figure 10:
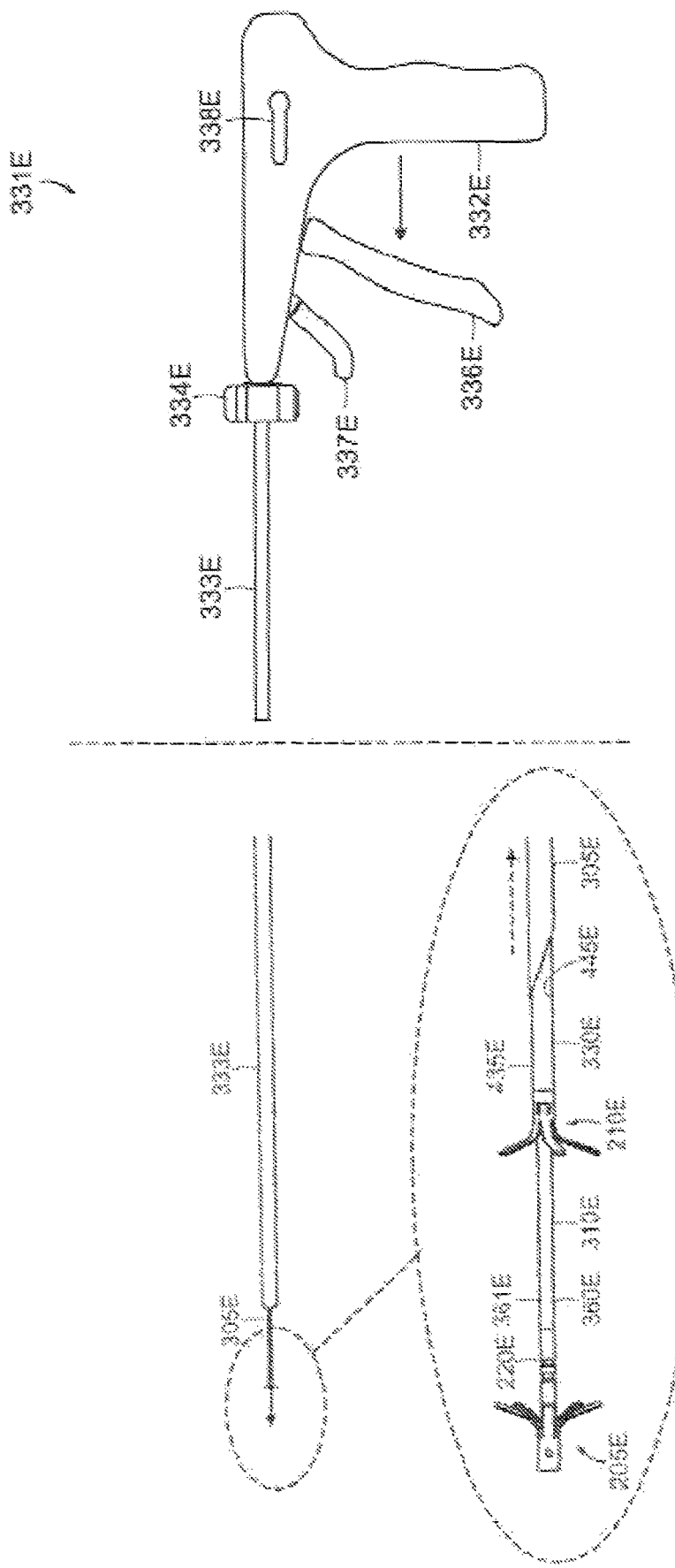

Then, with the deployed distal implant held in place by distal implant delivery tube 310E and its interlock with distal implant locking tube 220E, hollow needle 305E is withdrawn further proximally (e.g., via first trigger 336E) until proximal implant 210E is no longer constrained within hollow needle 305E (FIG. 10). As this occurs, legs 295E of proximal implant 210E are released from the constraint of hollow needle 305E and open radially.

Figure 11:
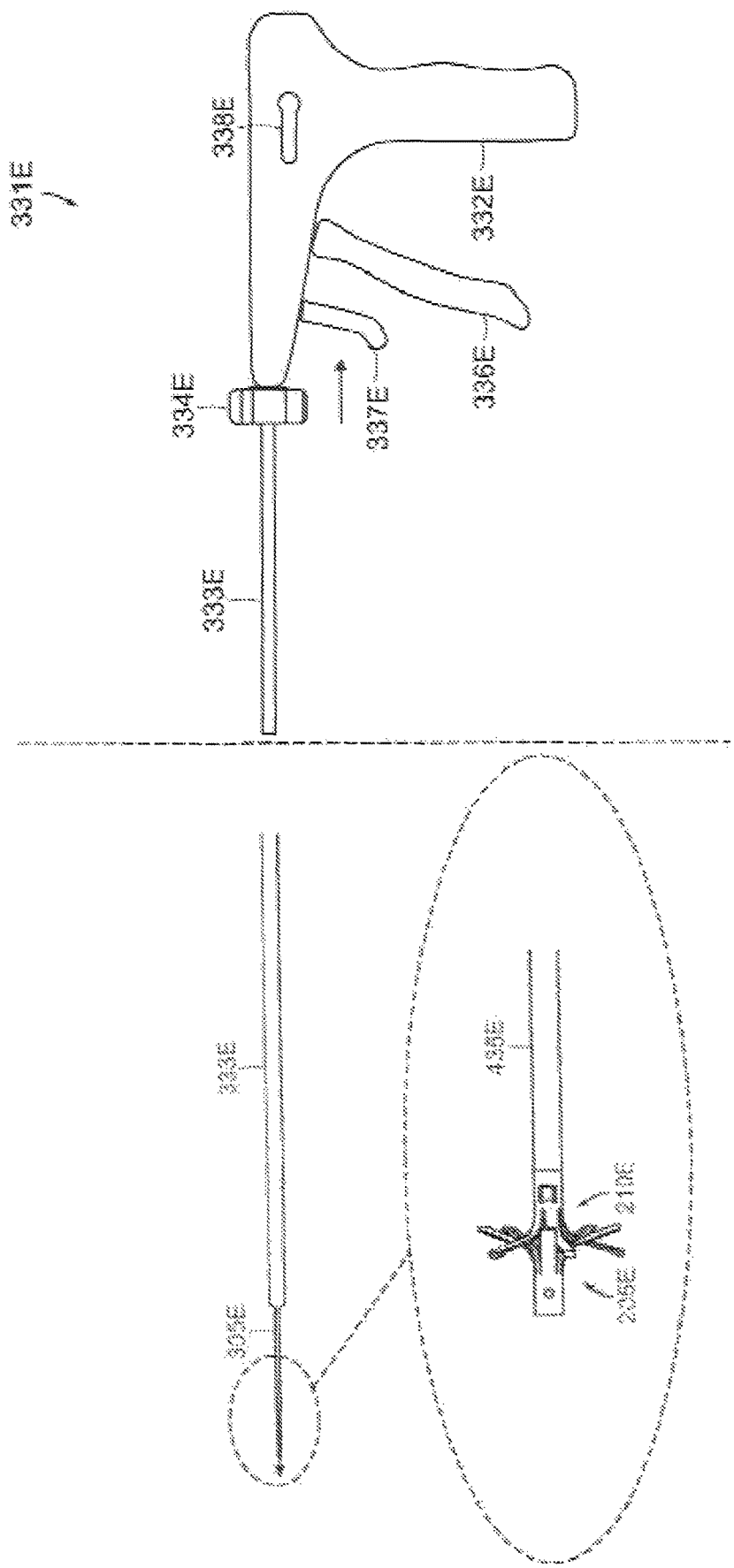

Proximal implant delivery tube 330E is then advanced distally, e.g., using second trigger 337E, until proximal implant 210E and distal implant 205E come together (FIG. 11). As distal implant 205E and proximal implant 210E move together, their legs 235E, 295E compress the blood vessel therebetween, thereby occluding the blood vessel. Distal implant 205E and proximal implant 210E continue moving together until inwardly-projecting tangs 300E of proximal implant 210E enter circumferential grooves or recesses 245E of distal implant 205E, thereby locking the two members into position relative to one another.

Figure 13:
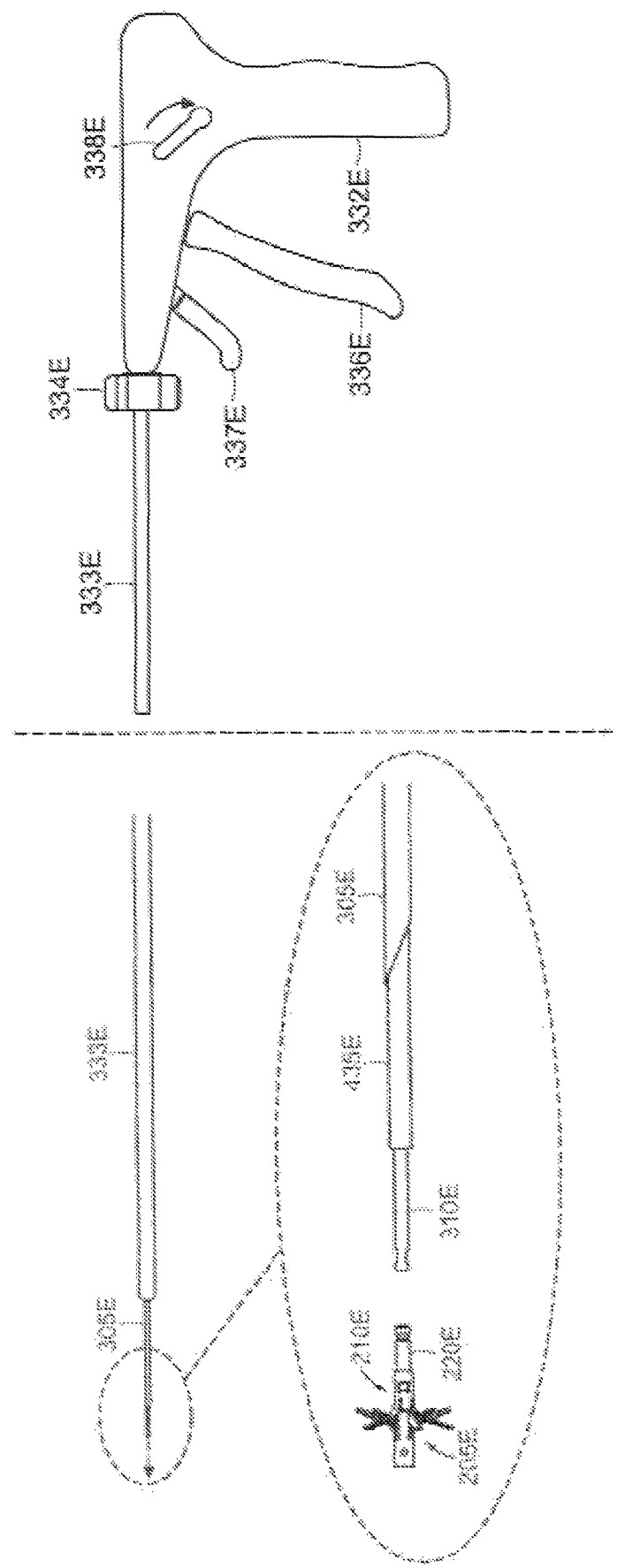
Figure 14:
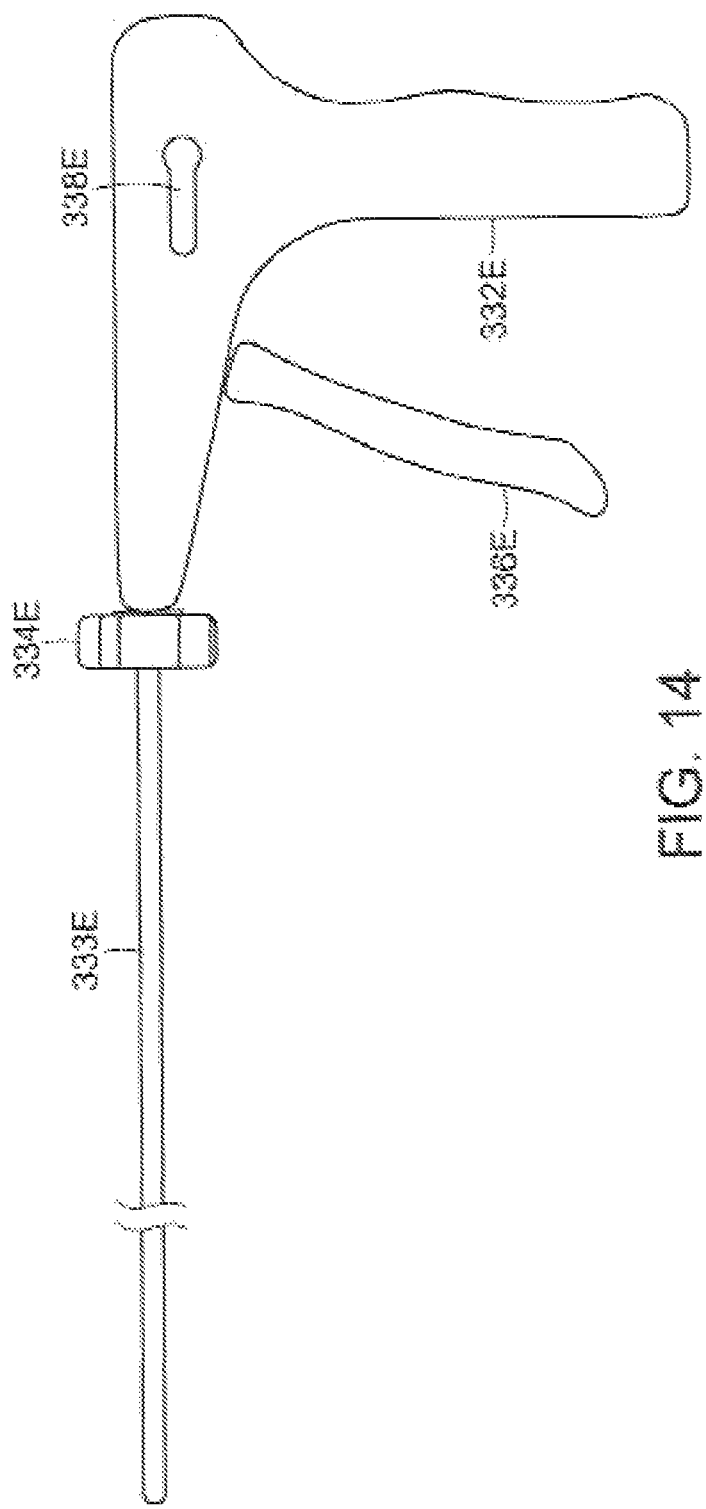
Figure 17:
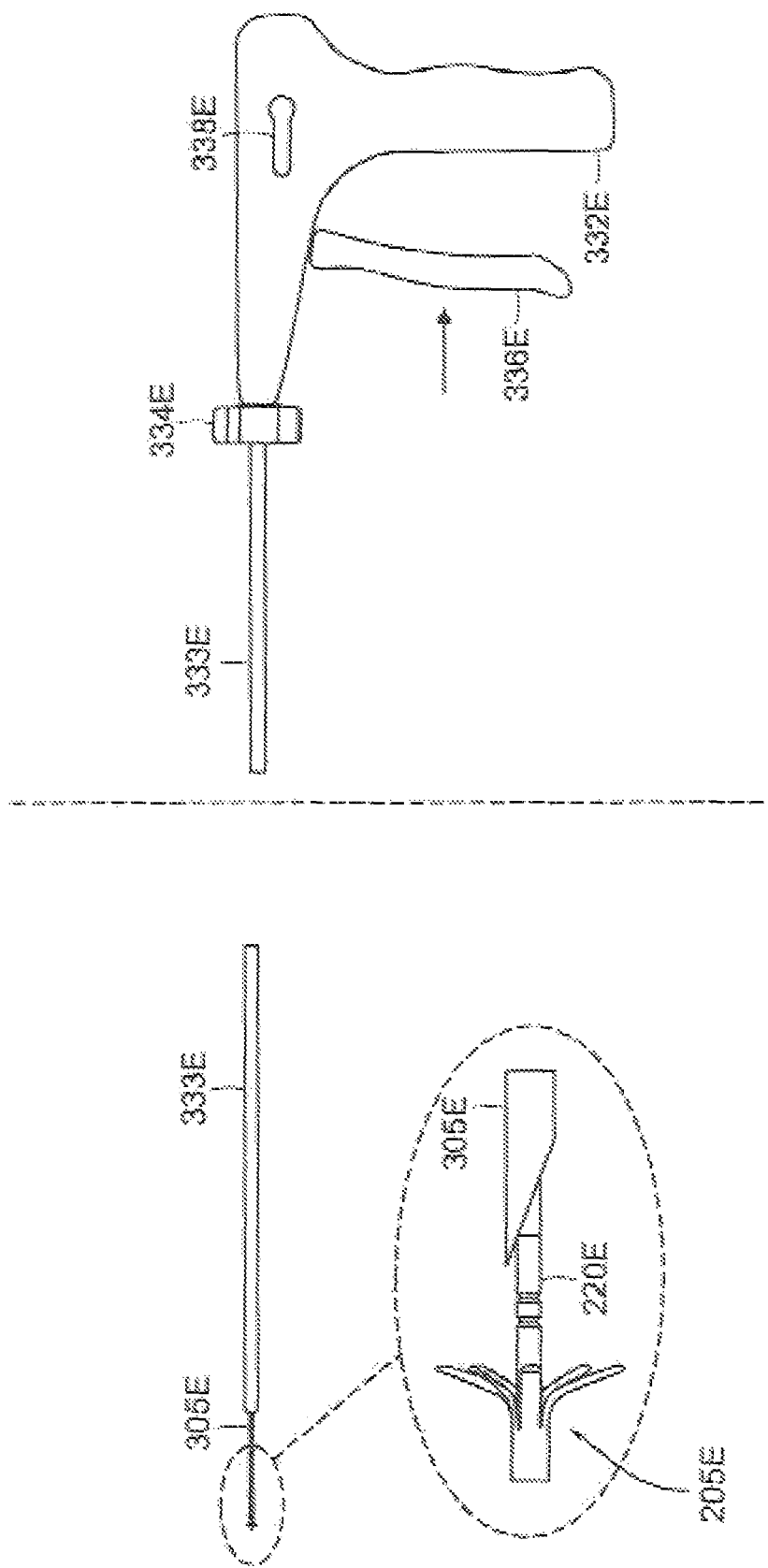
Figure 19:
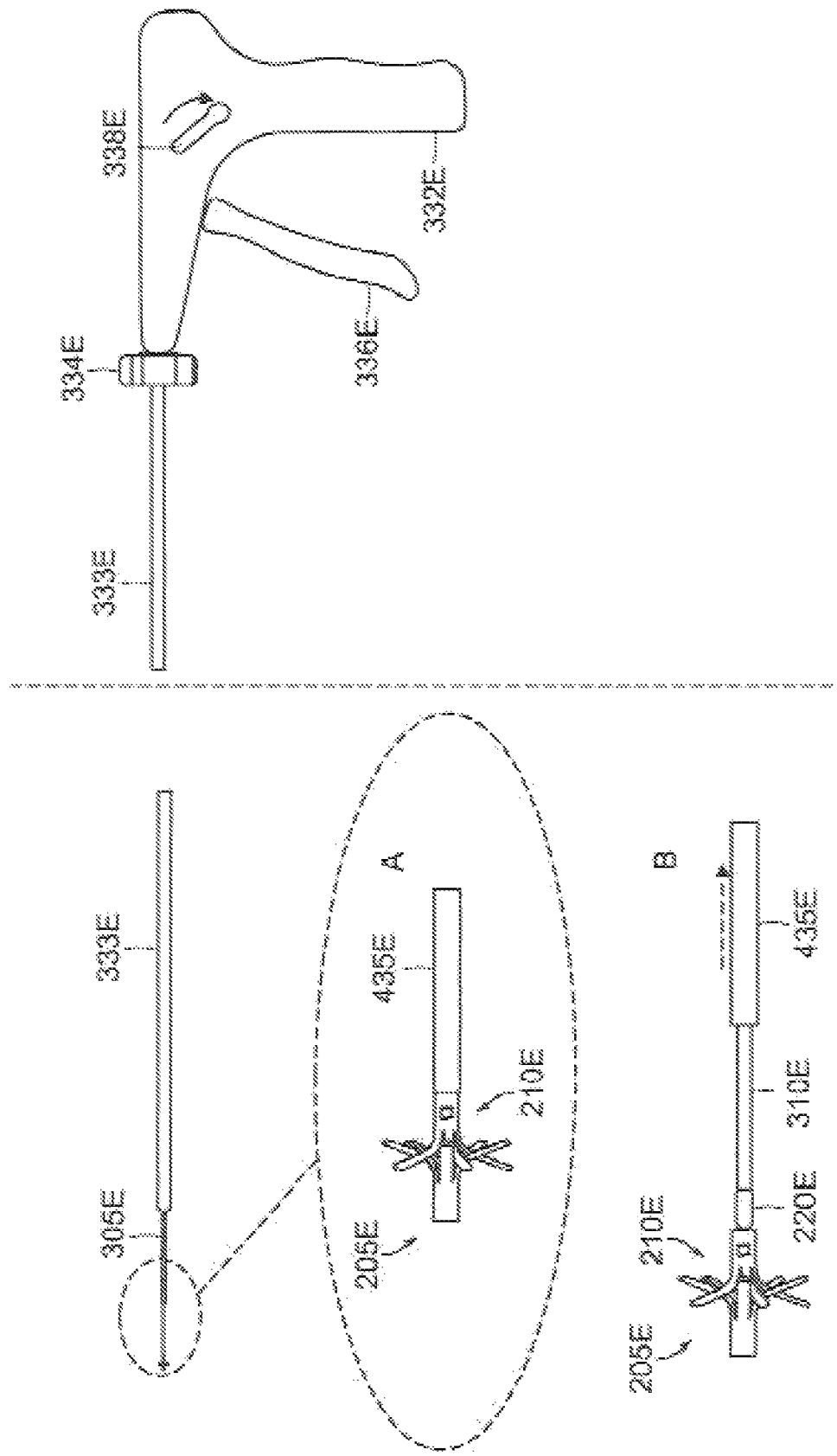
Figure 20:
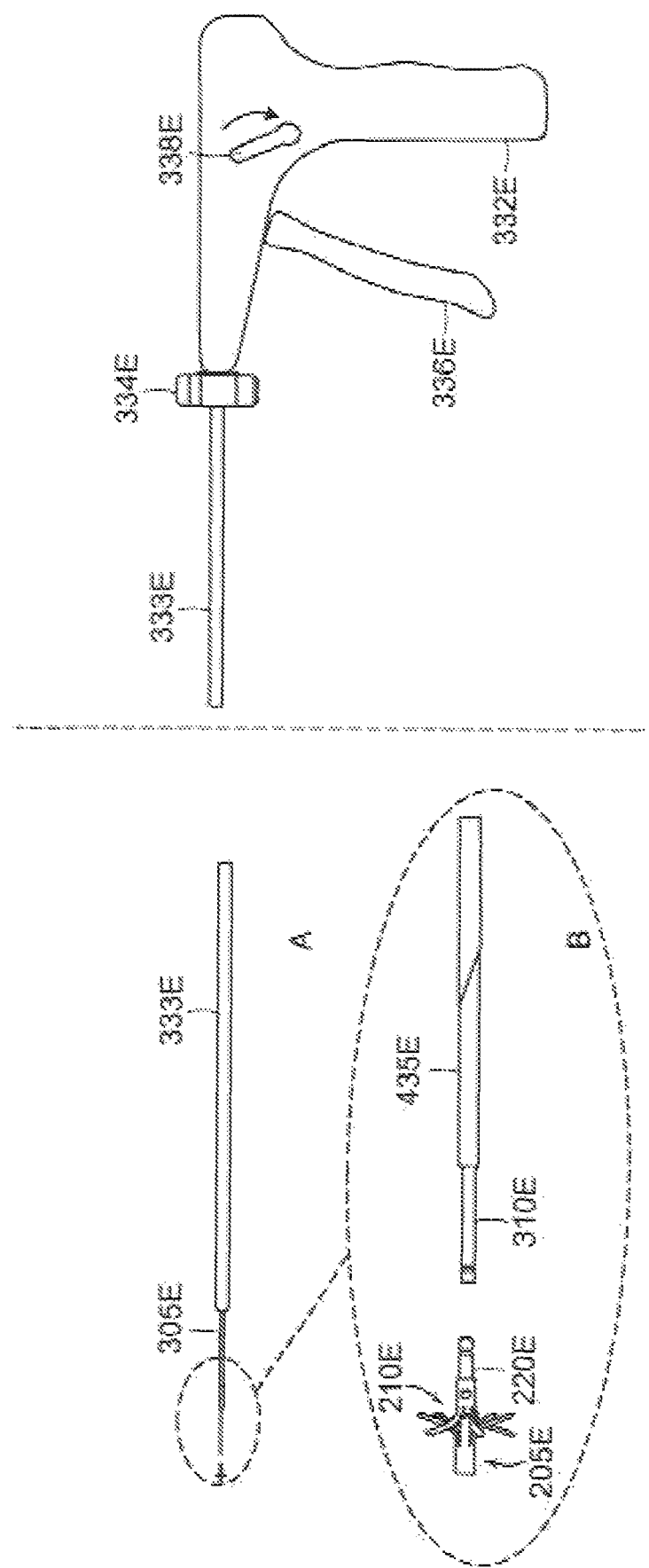
Figure 25:
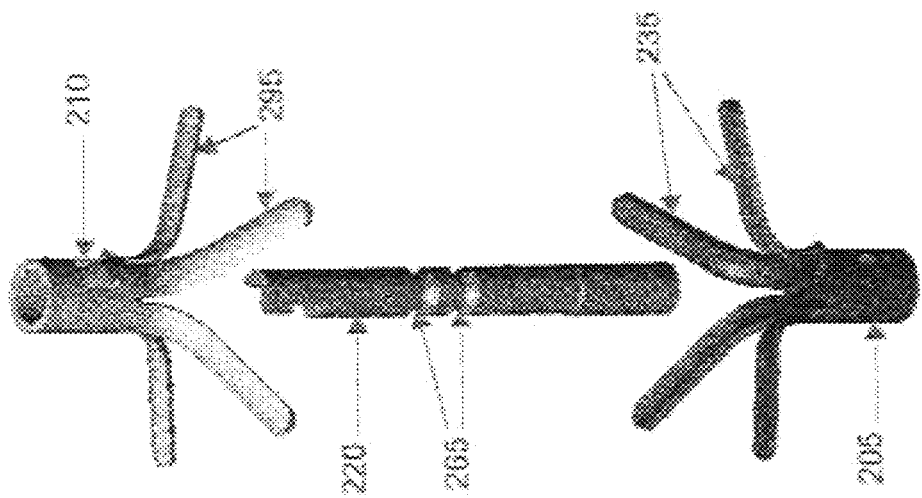
FIGS. 24-25 are schematic illustrations showing how the distal and proximal legs of the two-part fastener may be aligned with one another, or interdigitated between one another, when the two-part fastener is deployed.
Figure 24:
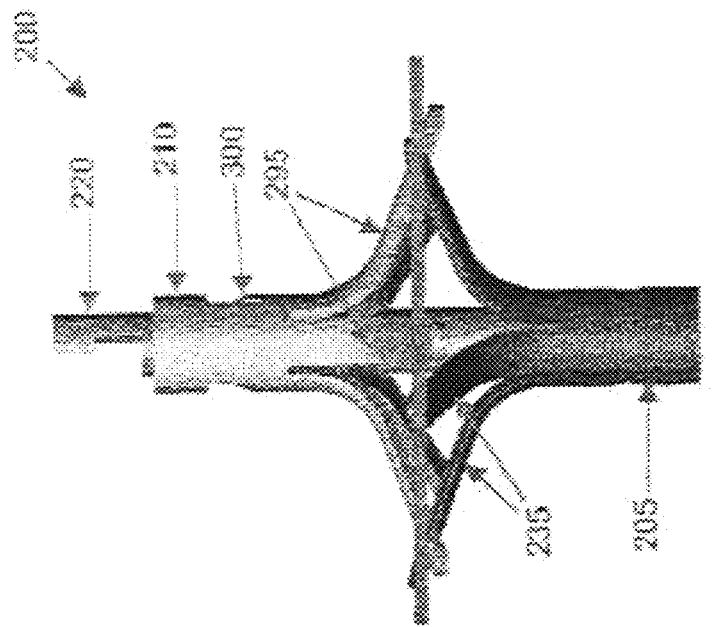
Figure 26:
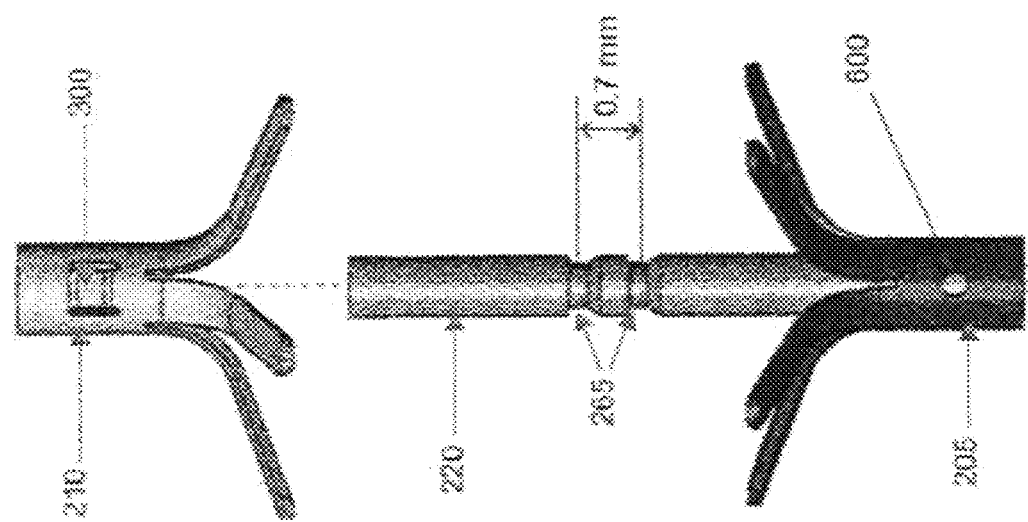
FIG. 26 is another view of the embodiment of FIG. 1
Figure 27:
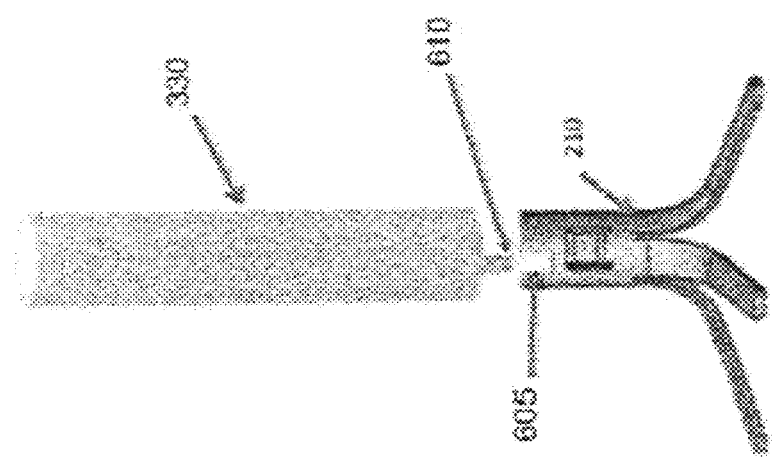
FIGS. 27-29 illustrate a modification in which the relative rotational orientation of the implants can be adjusted.
Figure 28:
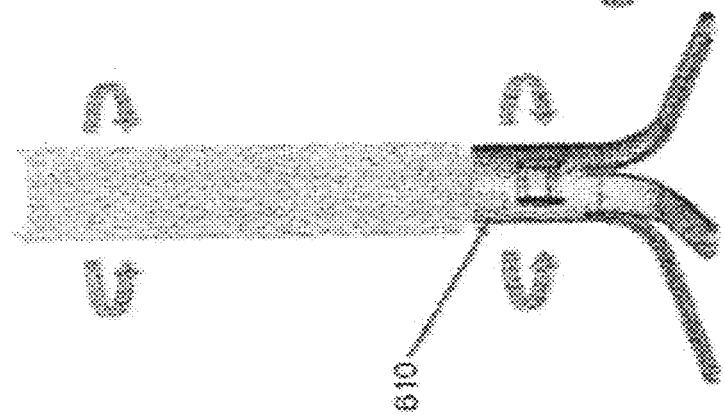
Figure 29:
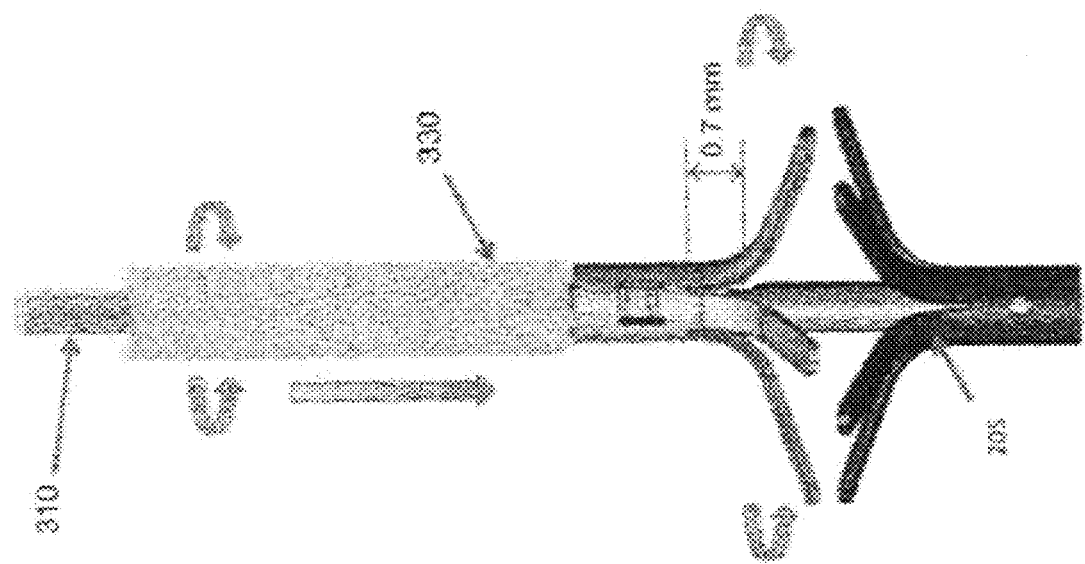
Figure 35:
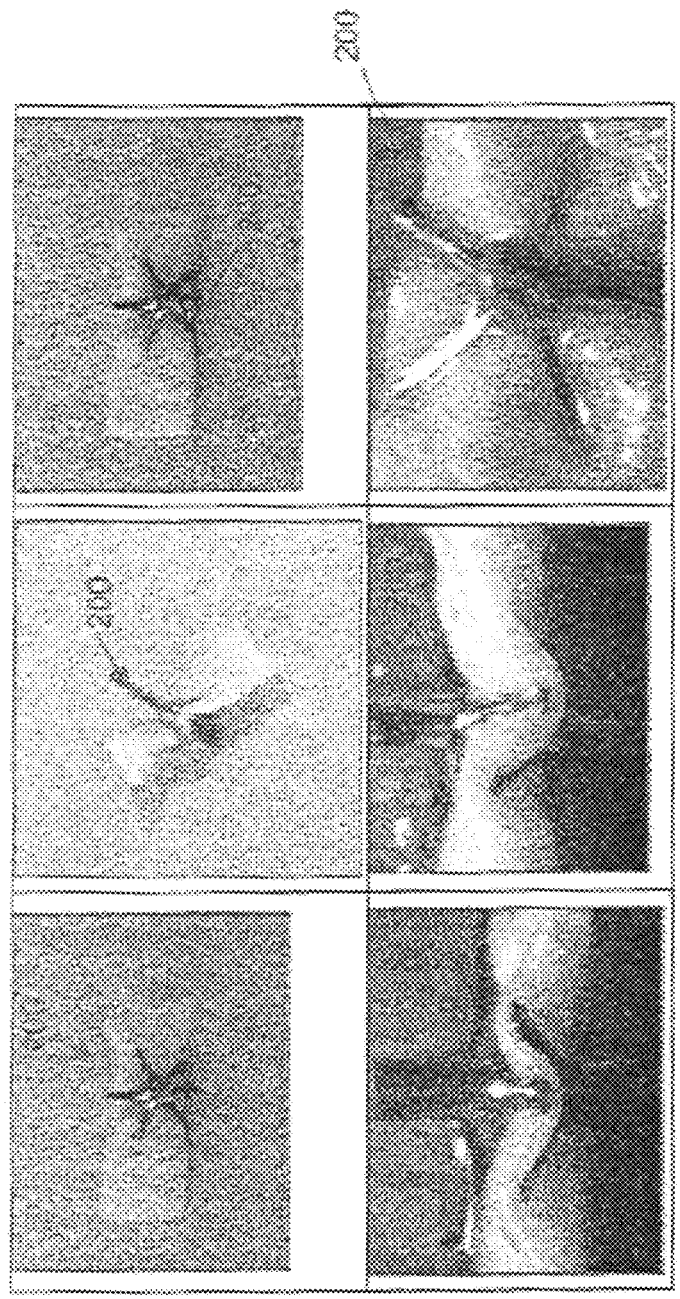
Figure 36:
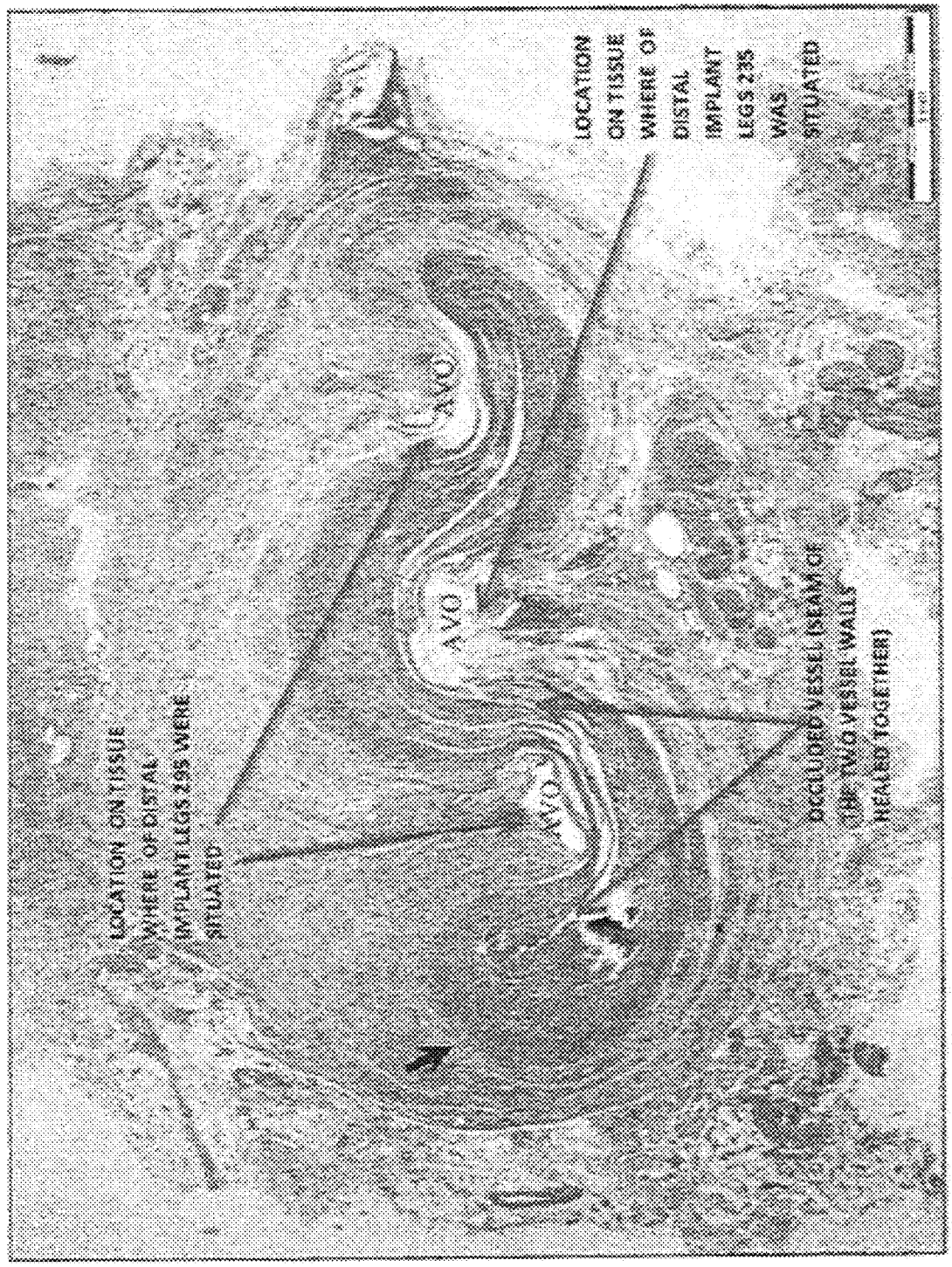
FIG. 36 is a photograph of a histological slide illustrating the serpentine configuration in which tissue layers have been constrained by a fastener in accordance with the invention.
Figure 37:
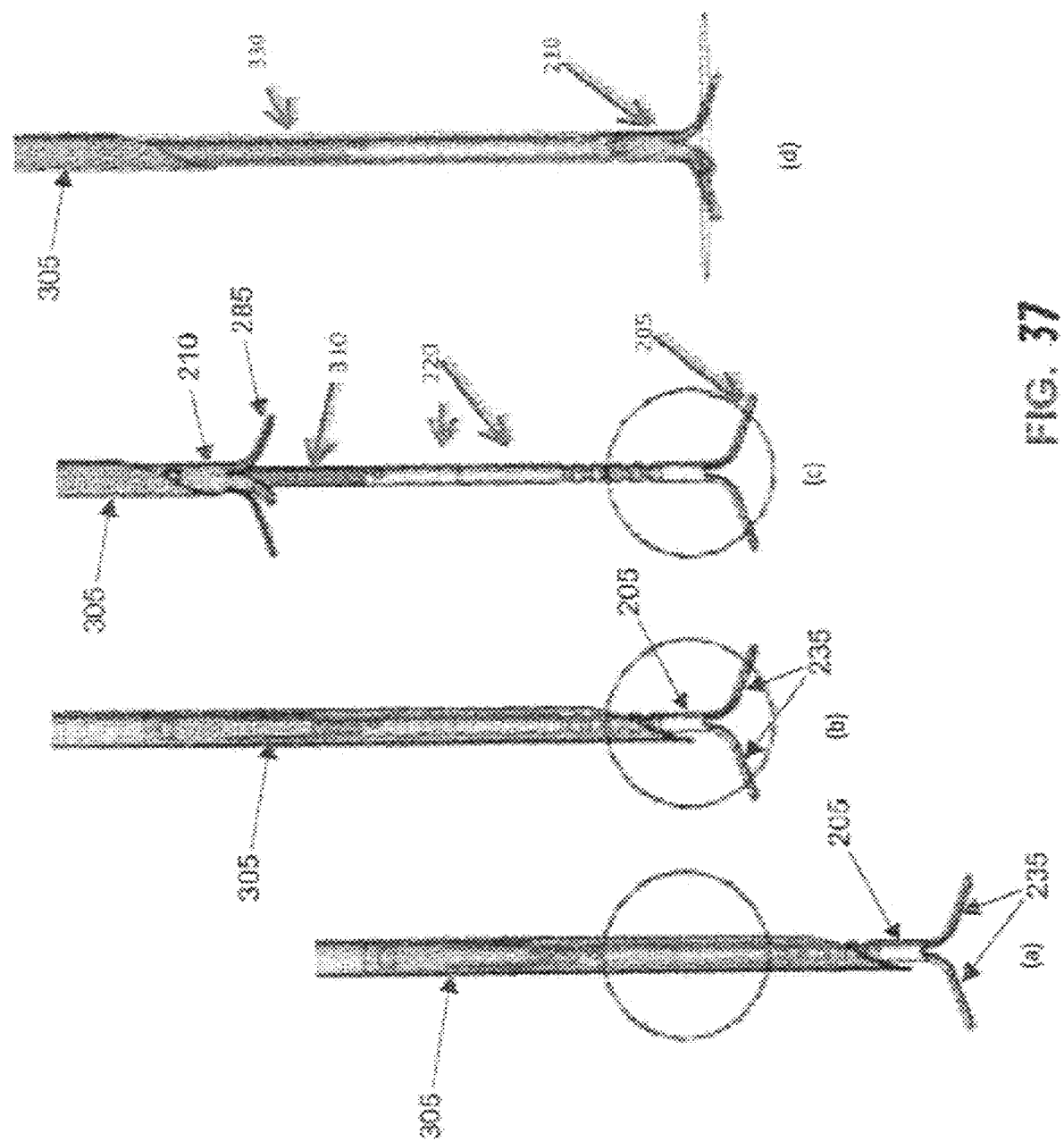
FIG. 37 is a sequential illustration of the arrangement for deploying an embodiment of the fastener.
Figure 39:
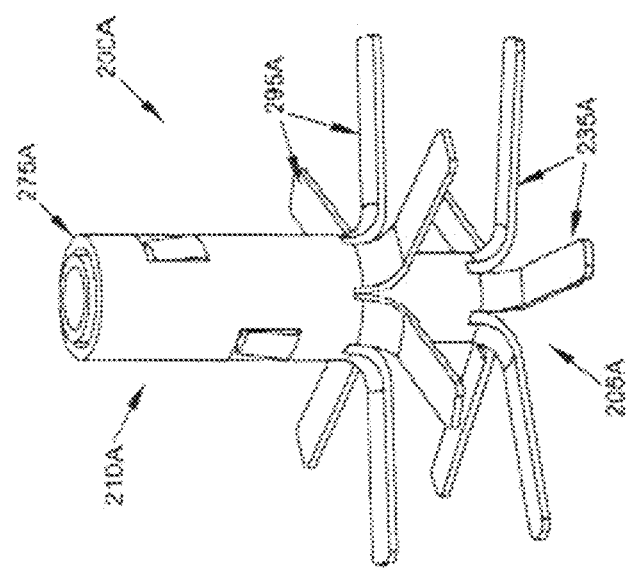
FIGS. 38-41 illustrate another embodiment of the two-part fastener.
Figure 38:
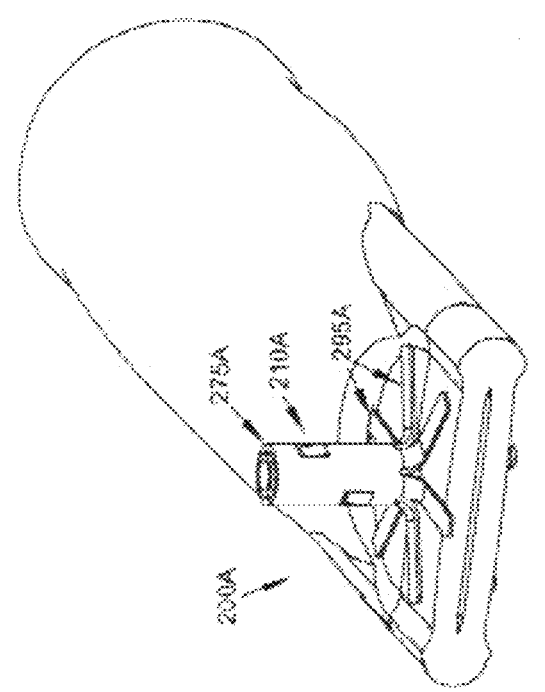
Figure 41:
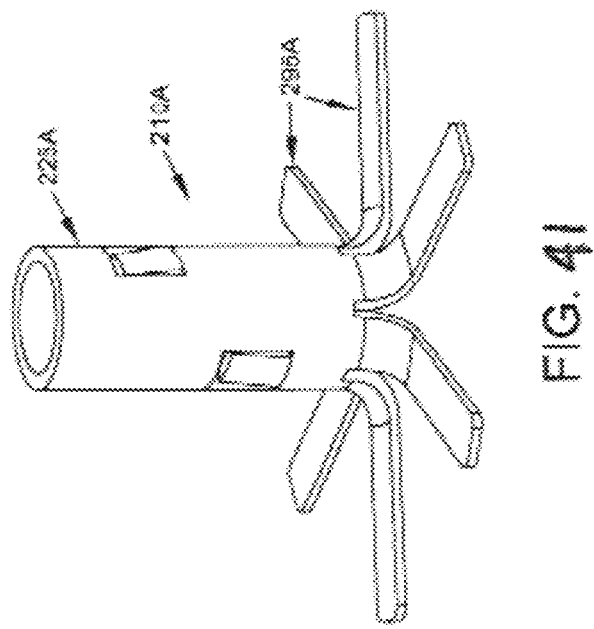
Figure 40:
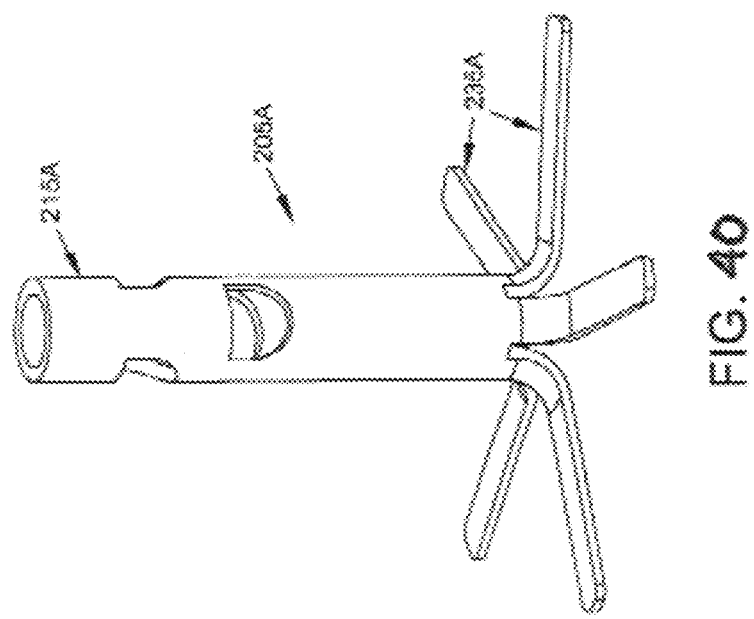
Figure 43:
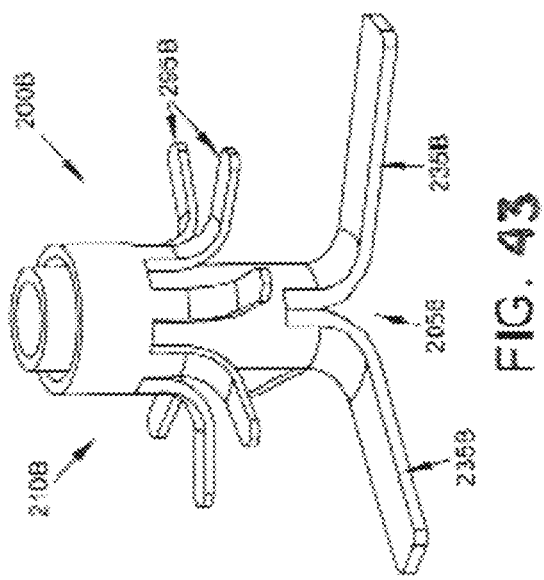
FIGS. 42-45 illustrate another embodiment of the two-part fastener.
Figure 42:
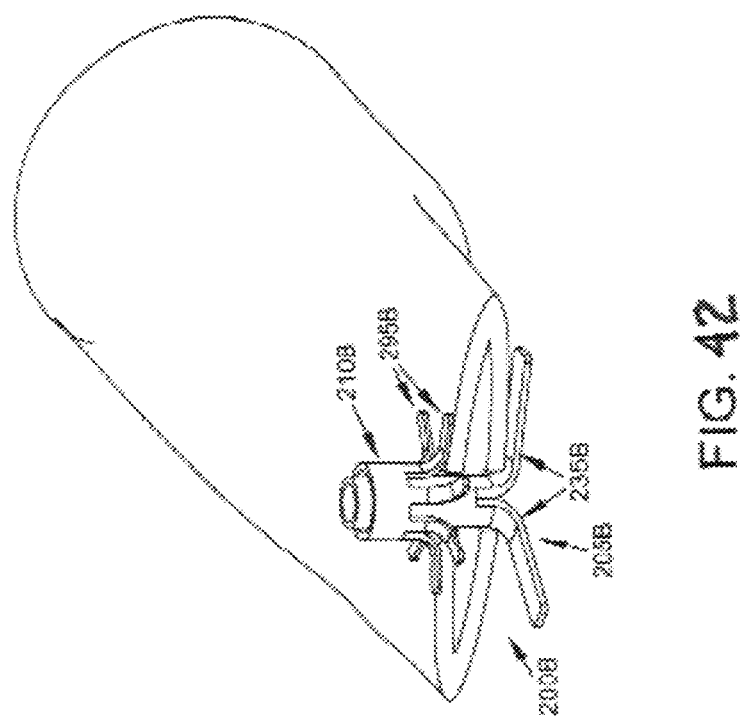
Figure 45:
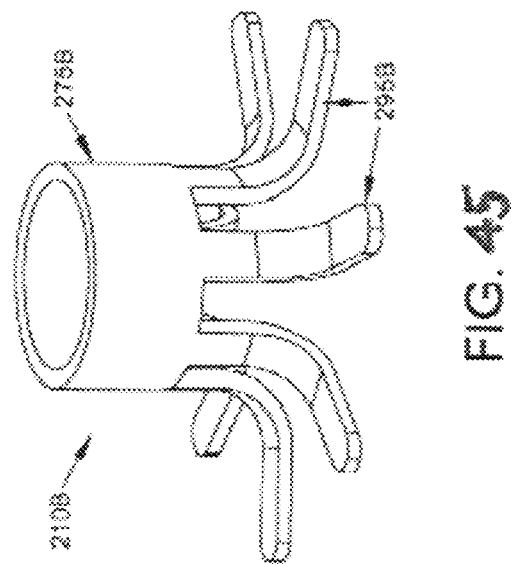
Figure 44:
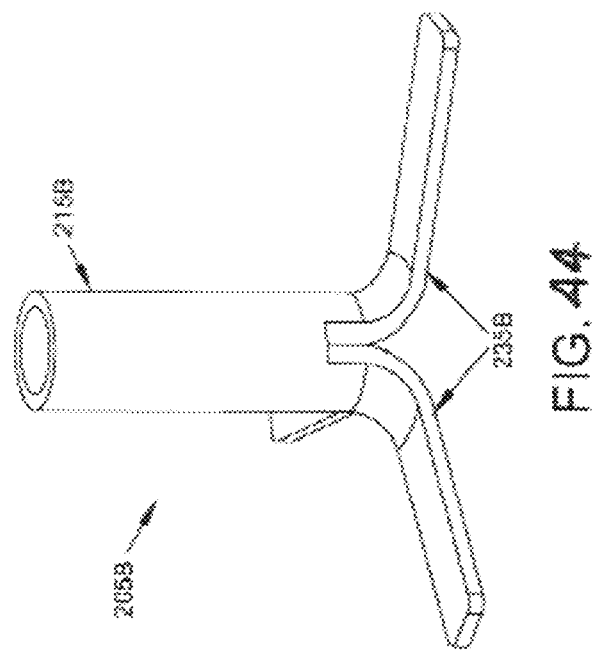

At this point, proximal implant delivery tube 330E is withdrawn (FIG. 12), distal implant delivery tube 310E is released from distal implant 205E (i.e., by using lever 338E to unlock the second half 361E of the mechanical interlock from the first half 266E of the mechanical interlock, and then the installation device is withdrawn (FIG. 13).

The foregoing procedure leaves two-part fastener 200E locked in position across the blood vessel, with the opposing legs 235E, 295E compressing the blood vessel therebetween, whereby to occlude the blood vessel.

The two-part fastener 200E is discussed above in the context of using the elasticity of its legs 235E, 295E to cause its legs 235E, 295E to reconfigure from a diametrically-reduced configuration (e.g., when constrained within a delivery needle) to a diametrically-expanded configuration (e.g., when released from the constraint of a delivery needle). However, it should also be appreciated that where legs 235E, 295E are formed out of a shape memory material (e.g., Nitinol), a temperature change may be used to reconfigure legs 235E, 295E from a diametrically-reduced configuration to a diametrically-expanded configuration. By way of example but not limitation, in this form of the invention, legs 235E, 295E may be constructed so as to have a diametrically-reduced configuration when maintained at a temperature below body temperature, and legs 235E, 295E may be constructed so as to have a diametrically-expanded configuration when maintained at body temperature. As a result, by cooling two-part fastener 200E to a temperature below body temperature, inserting the two-part fastener into the body, and then allowing the two-part fastener to heat to body temperature, legs 235E, 295E can be caused to reconfigure from their diametrically-reduced configuration to a diametrically-expanded configuration.

FIGS. 14-20 show an alternative form of installation device. The delivery device 331E shown in FIGS. 14-20 is generally similar to the laparoscopic device 331E shown in FIGS. 5-13, except that second trigger 337E is omitted, and lever 336E is used to both: (i) advance proximal implant delivery tube 330E until proximal implant 210E and distal implant 205E are drawn together, and (ii) release distal implant 205E from distal implant locking tube 220E (i.e., by unlocking the second half 361E of the mechanical interlock (carried by the distal end of distal implant delivery tube 310E) from the first half 266E of the mechanical interlock (carried by the proximal end of distal implant locking tube 220E)).

FIGS. 21-23 show another two-part fastener 200E also formed in accordance with the present invention. The fastener 200E shown in FIGS. 78-80 is substantially the same as the fastener 200E shown in FIGS. 58-77, except that legs 235E of distal implant 205E, and legs 295E of proximal implant 210E, have their concavities facing in the same direction, so that legs 235E, 295E nest with one another rather than facing each other.

Additionally, FIGS. 21-23 show in further detail the configuration of the mechanical interlock described above. More particularly, the first half 266E of the mechanical interlock on the proximal end of distal implant locking tube 220E comprises a stepped configuration 433E, and the second half 361E of the mechanical interlock on the distal end of distal implant delivery tube 360E comprises another stepped configuration 434E, wherein stepped configuration 433E and stepped configuration 434E are inverses of one another so as to mate together. After the second half 361E of the mechanical interlock has been secured to the first half 266E of the mechanical interlock, the connection between distal implant delivery tube 310E and distal implant 205E can be enhanced, e.g., by telescopically projecting a locking rod 436E through central lumen 437E of distal implant delivery tube 310E and into lumen 262E of implant locking tube 220E. In this form of the invention, the delivery device 331E may include appropriate control means (e.g., release lever 338E) for telescopically removing locking rod 436E.

It should also be appreciated that other forms of mechanical interlocks may be used for releasably securing distal implant 205E of the two-part fastener 200E of FIGS. 78-80 to distal implant delivery tube 310E. By way of example but not limitation, a screw interlock may be used, e.g., the first half 266E of the mechanical interlock (carried by the proximal end of distal implant locking tube 220E) may comprise a threaded bore, and the second half 361E of the mechanical interlock (carried by the distal end of distal implant delivery tube 360E) may comprise a threaded post, wherein the threaded post carried by the distal end of distal implant delivery tube 360E may be received in the threaded bore of distal implant locking tube 220E. Alternatively, other configurations of a screw interlock may be used, or other forms of mechanical interlocks may be used.

In the constructions shown in FIGS. 58-80, a mechanical interlock (e.g., a first half 266E carried by the proximal end of distal implant locking tube 220E and a second half 361E carried by the distal end of distal implant delivery tube 310E) is used to connect distal implant locking tube 220E (and hence distal implant 205E) to distal implant delivery tube 310E. Alternatively, if desired, distal implant locking tube 220E can be formed integral with distal implant delivery tube 310E, with a weakened section disposed at their intersection, and the two members separated by a mechanical breaking action.

FIGS. 38-41 illustrate another two-part occluder 200A having a distal implant 205A and a proximal implant 210A. Two-part occluder 200A is generally similar to the aforementioned two-part occluder 200, except that distal implant 205A utilizes a unibody construction.

FIGS. 42-45 illustrate another two-part occluder 200B. Two-part occluder 200B is generally similar to the aforementioned two-part occluder 200A, except that distal implant 205B utilizes a friction fit to lock distal implant 205B to proximal implant 210B.

Temporary Blood Vessel Occlusion for Extremity Trauma

Uncontrolled hemorrhage remains the most significant cause of death in victims who survive a major initial trauma, particularly in truncal and extremity injuries. A loss of 50% of blood volume without replenishment is frequently fatal, and a hypotensive patient, who has lost 30%-35% of blood volume and is in uncompensated shock, is generally close to death.

Establishing and maintaining hemostasis at the site of an injury is an important consideration in the acute management of trauma patients. The tourniquet, with or without local compression, remains the time-honored method for controlling extremity bleeding following trauma. However, tourniquets are generally only useful for controlling bleeding in limbs, and even then tourniquets suffer from the disadvantage that they limit blood flow to the entire limb and cannot target individual blood vessels within the limb. It is estimated that of all military wounded whom ultimately succumb to their wounds, approximately 10-20% die from blood loss due to inadequate compression or tourniquet application.

Thus there is also a need for effective temporary blood vessel occlusion for military and civilian trauma cases.

In addition to trauma applications, there are many instances where an occlusion device may be implanted and then, at a later time (e.g., days, months, years), may be removed. Examples of such uses of temporary occlusion devices include reversible occlusion of fallopian tubes, temporary occlusion of the saphenous vein during pregnancy and subsequent removal of the occlusion device at the conclusion of pregnancy so as to restore blood flow through, etc.

The present invention also envisions deployment of temporary occlusion devices that can provide an option to the clinician to leave the fastener/occluder in the body permanently.

The present invention also provides a novel temporary occlusion device (hereinafter sometimes referred to as a "temporary occluder") that can be deployed percutaneously to temporarily occlude major blood vessels, particularly arteries until specialized care can be obtained to surgically control massive hemorrhage following civilian or military trauma. The novel temporary occluder of the present invention may be used as an alternative to a conventional tourniquet to control major extremity bleeding following trauma, providing a more effective, reliable and highly targeted method to control major blood vessel hemorrhage. Furthermore, unlike a conventional tourniquet, the temporary occluder of the present invention may be used even in the presence of soft tissue injury. Once deployed, minimal post-deployment supervision is required during the time required to transport the patient to the specialized care required to surgically repair the damaged blood vessel and traumatized region. The present invention requires accessing the damaged blood vessel (e.g., major artery) with a needle or other device utilizing portable ultrasound to visualize, identify and access the region of the damaged blood vessel significantly simplifies the temporary occlusion procedure. Deployment comprises passing a portion of the temporary occluder across the artery so that a distal portion of the temporary occluder bears against the outside surface of the blood vessel on the far (distal) side of the blood vessel, and positioning a proximal portion of the temporary occluder against the outside surface of the blood vessel on the near (proximal) side of the blood vessel, or against the outside surface of the skin, whereby to establish an occluding compression across the blood vessel. Once deployed, removal of the temporary occluder may be performed in the specialized care center at the appropriate time. Following removal of the temporary occluder, hemostasis of the punctures caused by deployment of the temporary occluder across the blood vessel may be obtained with standard manual compression of the blood vessel, thus minimizing the need for further blood vessel repair. Alternatively, other means such as cauterization of the tissue, deploying a polymeric sealant, or deploying gauze or a pad, or positioning a coated stent in the vessel, may be used to arrest blood flow.

The distal occluder 515 and proximal occluder may be formed similarly to the implants described above from a Nitinol cylinder having distal slits formed therein, whereby to form cylindrical body 525 and laterally-expandable legs 530 540, respectively. In one embodiment, each laterally-expandable legs 530, 540 may be designed with an appropriate length to minimize unnecessary penetration into any tissues which may reside adjacent to the blood vessel. In one embodiment, each laterally-expandable leg 530, 540 is less than about 20 mm in length. Preferably, the cylindrical bodies 525, 535 are both less than about 18 gauge. Distal portion 515 is sized to be concentrically received within proximal portion 520.

Figure 50:
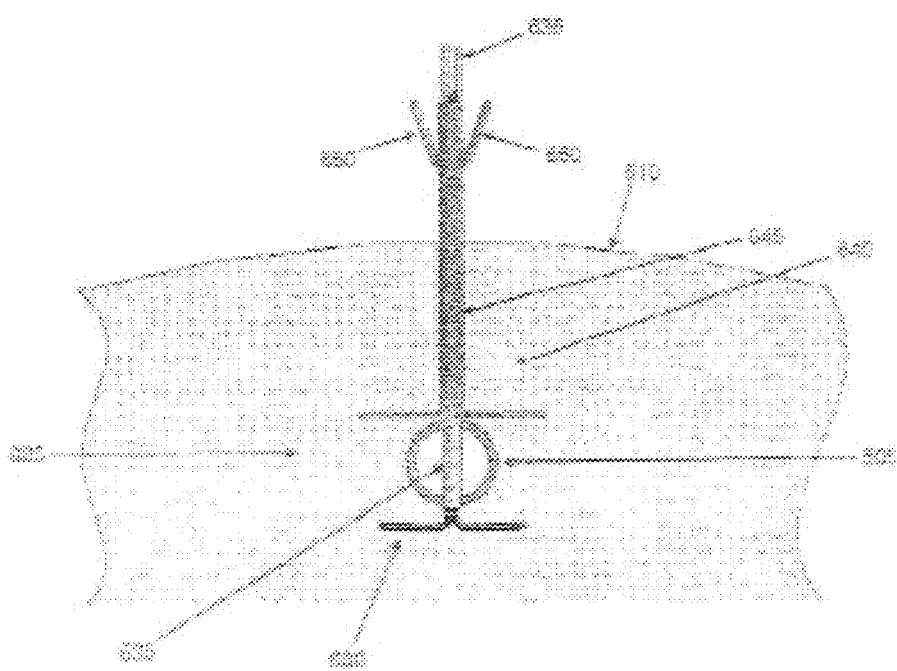
FIGS. 50-51 illustrate another embodiment of the two-part, temporary occlusion device.
Figure 51:
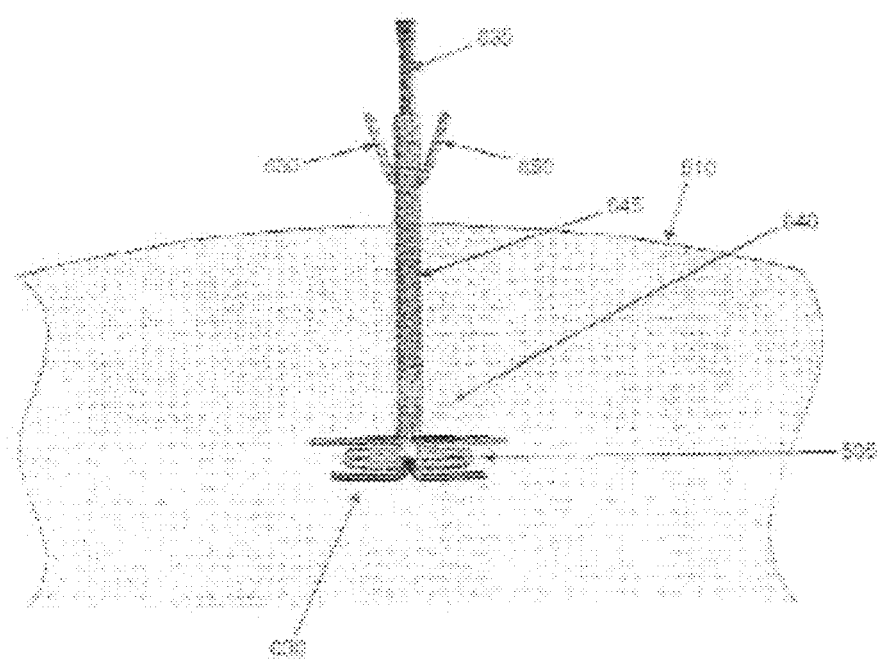

FIGS. 50 and 51 show a temporary occluder 625 which comprises another form of the two-part invention. Temporary occluder 625 may have proximal and distal self-expandable legs is substantially the same as the two-part occluder 200A, except that (i) temporary occluder 625 comprises a distal implant 630 having an elongated distal implant body 635 of increased length sufficient to extend through the tubular body of the proximal implant 645 and protrude above the surface of skin 510, and a proximal implant 640 having a proximal implant body 645 of increased length sufficient to also protrude above the surface of skin 510. Temporary occluder 625 also comprises fingers 650 on proximal implant body 645 that cooperate with tubular body of the distal implant 630 to lock the relative positions of the implants in any of a plurality of relative positions, thereby enabling the degree of compression of the vessel to be varied to control blood loss while also avoiding hemostasis and potential blood clots. The fingers may be operated to disengage the proximal and distal implants.

Figure 52:
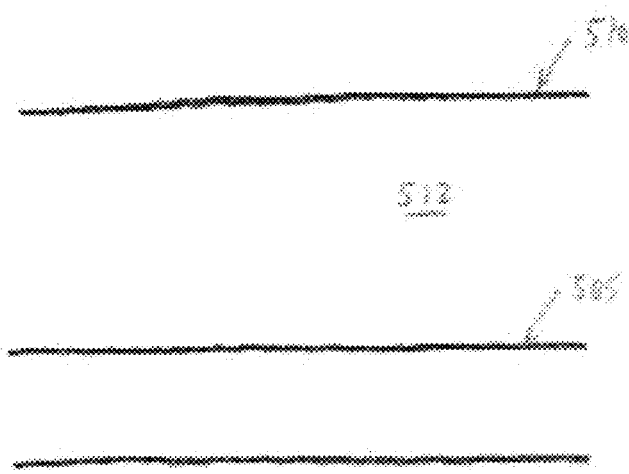
FIGS. 52-59 illustrate additional embodiments of temporary occlusion devices.
Figure 53:
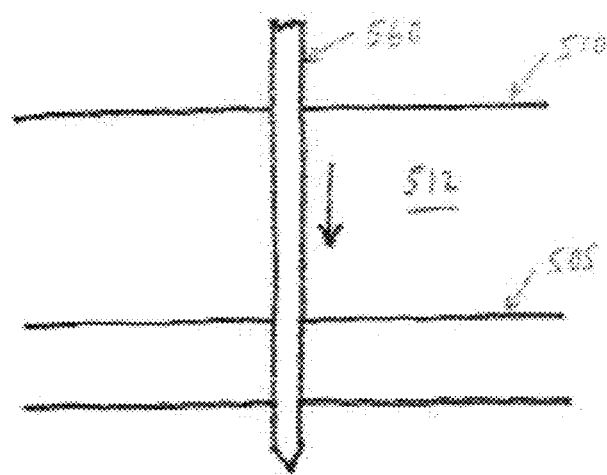
Figure 54:
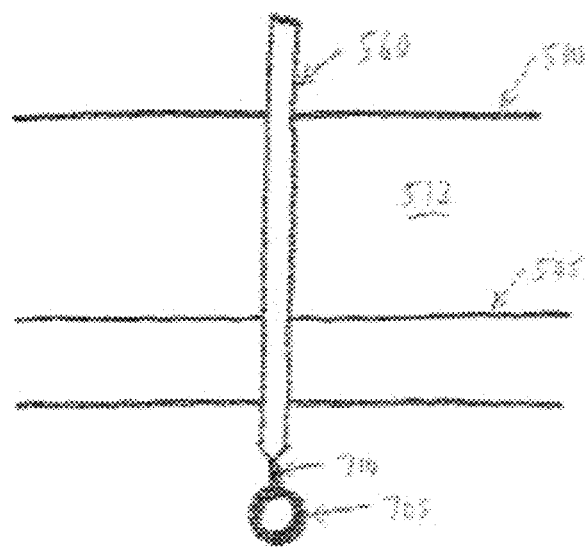
Figure 55:
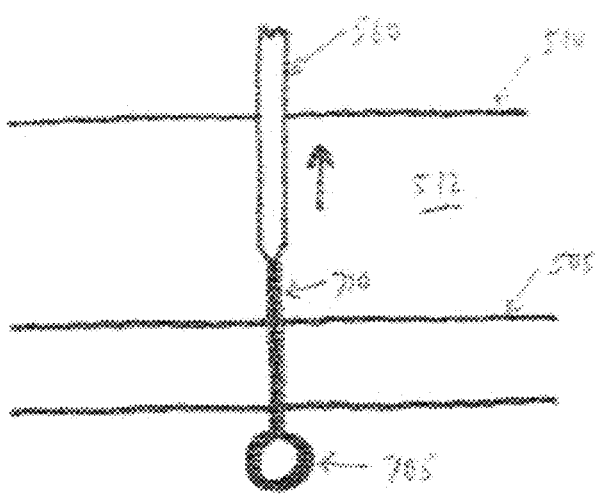
Figure 56:
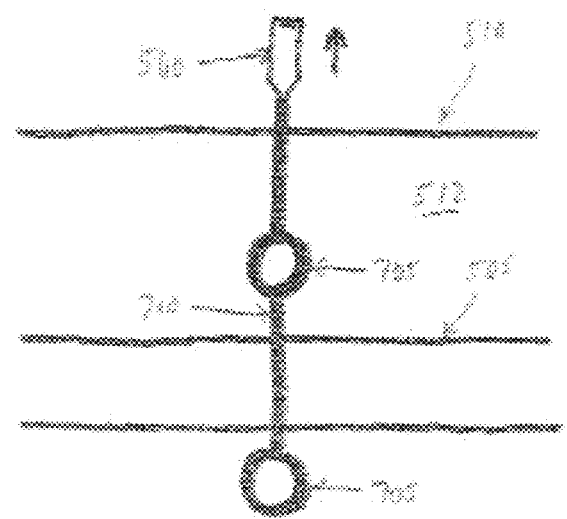
Figure 57:
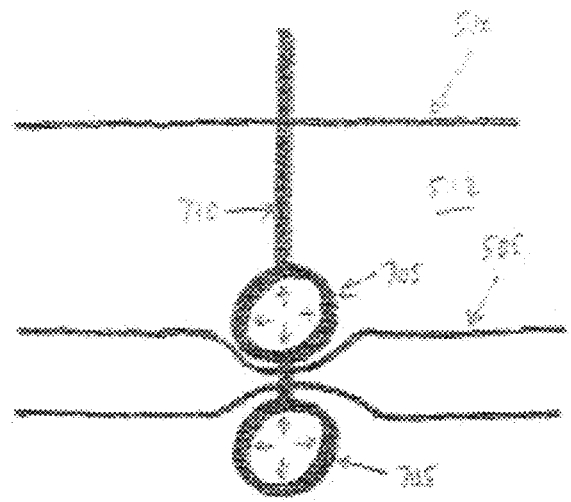

FIGS. 52-59 show, diagrammatically, another form of temporary occluder that includes a pair of balloons 705, which may be made of a compliant polymer (e.g., latex or silicone) or non-compliant (e.g., polyethylene terephthalate), or a thin metal or other material. The balloons are mounted in longitudinally spaced relation along a shaft 710 and may be inflatable simultaneously or separately by one or two inflation lumens formed through the shaft. The spacing between the balloons preferably is of the order of one-half to one centimeter so that they can be positioned on opposite sides of a target vessel and the inflated to effect compression of the vessel between the balloons. The balloons and shaft should be formed so that when in deflated configuration they can passed through the lumen of the delivery needle. The lumens may be concentric or may be formed side-by-side and in parallel within the shaft. In use, and as seen in FIGS. 52 and 53, a needle 560 is passed through the skin 510, through intervening tissue 512 and through a target blood vessel 505 (FIG. 54). With the distal end of the needle distally of the vessel, the occluder may be advanced to advance the distal balloon 705 out of the needle, as by retracting the needle 560 or pushing the shaft through the needle (FIG. 55). The shaft 710 should have sufficient column strength to allow it to be advanced through and out of the needle without buckling. With the distal balloon positioned distally of the vessel, the needle may be retracted to expose the proximal balloon on the proximal side of the vessel (FIG. 56). The balloons then can be inflated simultaneously or separately, a desired by the clinician thereby to occlude blood vessel 505 (FIG. 57). In any of the balloon embodiments, the degree of vessel occlusion can be controlled by controlling the balloon inflation pressure.

In a variant of the invention each balloon may be formed on a separate concentric inner and outer shafts, each of which has its separate inflation lumen and with the inner shaft being movable within the outer shaft. Each shaft has an inflation lumen to allow the balloons to be inflated separately or simultaneously, as desired. With this embodiment the spacing of the balloons can be adjusted by the clinician.

When temporary occlusion is to be withdrawn, balloons 705 are deflated and then the two balloons are pulled free of the anatomy by pulling proximally on shaft 710.

Figure 58:
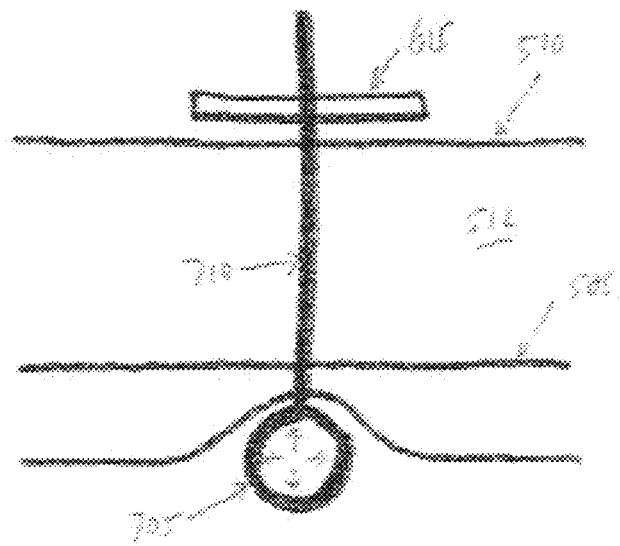

In another form of the invention, and looking now at FIG. 58, a balloon 705 may be positioned on the far side of the blood vessel, a cap 615 may be positioned about inflation line 710 at the surface of skin 510, balloon 705 may be inflated and then tension pulled between inflated balloon 705 and cap 615 so as to occlude blood vessel 505.

When temporary occlusion is to be withdrawn, balloon 705 is deflated using inflation line 710, and then balloon 705 is pulled free of the anatomy by pulling proximally on inflation line 710.

Figure 59:
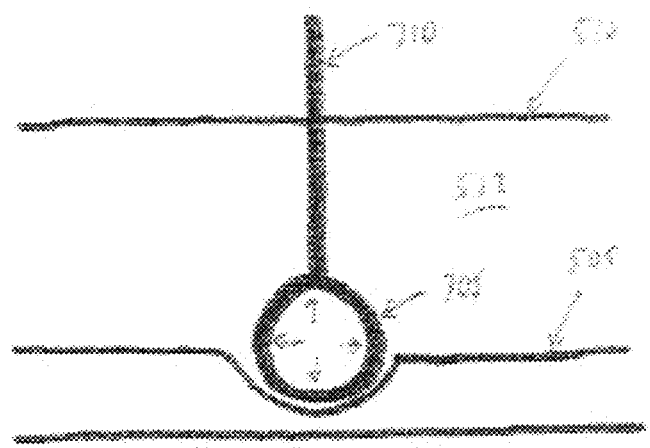

In still another form of the invention, as shown diagrammatically FIG. 59, a balloon 705 may be positioned on the near side of the blood vessel, and then inflated using inflation line 710 so as to bear against blood vessel 505 and thereby occlude the blood vessel. Thus, in this form of the invention, temporary occlusion can be achieved without penetrating the blood vessel.

When temporary occlusion is to be withdrawn, balloon 705 is deflated using inflation line 710, and then balloon 705 is pulled free of the anatomy by pulling proximally on inflation line 710.

The balloon(s) 705 may be filled with air, water or a compound of higher molecular weight than air. The balloon 705 may also be inflated with a polymer that hardens in situ, for applications where it is desirable to permanently maintain occlusion of the blood vessel. Alternatively, balloon 705 may be inflated with a polymer that hardens in situ and thereafter bio-degrades over time. In each of these balloon embodiments, the degree of occlusion can be adjusted by adjusting the positions or degree of inflation of the balloons.

In another embodiment of the present invention, the occluder may comprise a sealed tube having two regions that may be inflated into balloons. These balloon regions are expanded using air or liquid pressure.

In the foregoing disclosure, there is described an occluder (permanent or temporary, utilizing various constructions) which occludes a hollow structure (e.g., a blood vessel). In this respect it should be appreciated that the occluder may be positioned directly against a surface (e.g., an outer surface) of the hollow structure, or the occluder may be positioned such that an intervening structure or structures (e.g., anatomical tissue) may reside between the occluder and the hollow structure which is to be occluded. In this latter situation, the occluder applies a force to the intervening structure or structures, whereby to occlude the hollow structure which is to be occluded.

Using the Temporary Occluder to Occlude Tubular Structures Other than Blood Vessels It will be appreciated that the temporary occluder of the present invention can also be used to occlude tubular structures other than blood vessels. By way of example but not limitation, the temporary occluder of the present invention can be used to occlude other hollow anatomical structures within the body such as fallopian tubes and/or vas deferens for temporary or permanent sterilization, ducts such as bile ducts and cystic ducts for cholecystectomy, lymphatic vessels, including the thoracic duct, fistula tracts, etc.).

MODIFICATIONS OF THE PREFERRED EMBODIMENTS

It should be understood that many additional changes in the details, materials (e.g., shape memory polymers that are permanent or that dissolve over time), steps and arrangements of parts, which have been herein described and illustrated in order to explain the nature of the present invention, may be made by those skilled in the art while still remaining within the principles of the invention.

The invention claimed is:

1. An apparatus for securing a tissue layer to another tissue or non-tissue layer together comprising:
    a hypodermic needle having a lumen dimensioned to accommodate a tubular member no larger than about 18 gauge;
    a distal implant contained within the lumen and comprising a tubular distal body and a plurality of legs which may assume (i) a diametrically-reduced delivery configuration and (ii) a diametrically-expanded deployed configuration in which the legs are extended radially of the distal body; and
    a proximal implant, separate from the distal implant and contained within the lumen proximally of the distal implant, the proximal implant comprising a tubular proximal body and a plurality of legs configured to assume (i) a diametrically-reduced delivery configuration and (ii) a diametrically-expanded deployed configuration in which the legs are extended radially of the proximal body;
    the proximal and distal implants being ejectable, out of the needle, separately of each other; and
    wherein the proximal and distal implants are connectible together after ejection, the radially extended configuration of the legs being constructed and arranged so that when the proximal and distal implants are connected together, legs of the proximal and distal implants are interdigitated in the absence of the tissue or non-tissue layers between the proximal and distal implants.

2. The apparatus of claim 1, wherein the apparatus comprises a shape memory material and where the legs of each of the proximal and distal implants self-expand upon release of each implant from its delivery configuration.

3. The apparatus of claim 1 wherein the legs of at least one of the proximal and distal implants, when diametrically expanded, together define a concave configuration.

4. The apparatus of claim 1, wherein the distal implant legs together form a concave configuration when diametrically expanded, and the proximal implant legs together form a concave configuration when diametrically expanded.

5. The apparatus of claim 4 wherein the concave configuration of the legs of the proximal implant faces the concavity of the distal implant.

6. The apparatus of claim 4 wherein the concavities of both proximal and distal implants face in a distal direction.

* * * * *